US012805751B2

(12) United States Patent
Sacks et al.

(10) Patent No.: US 12,805,751 B2
(45) Date of Patent: Nov. 24, 2026

(54) DEVICES AND SYSTEMS FOR PREVENTING THE DEVELOPMENT OF PRESSURE ULCERS

(71) Applicants: Washington University, St. Louis, MO (US); Northwestern University, Evanston, IL (US)

(72) Inventors: Justin Sacks, St. Louis, MO (US); Matthew MacEwan, St. Louis, MO (US); John Rogers, Evanston, IL (US)

(73) Assignees: Washington University, St. Louis, MO (US); Northwestern University, Evanston, IL (US)

( * ) Notice: Subject to any disclaimer, the term of this patent is extended or adjusted under 35 U.S.C. 154(b) by 507 days.

(21) Appl. No.: 18/257,221

(22) PCT Filed: Dec. 14, 2021

(86) PCT No.: PCT/US2021/063277

§ 371 (c)(1),
(2) Date: Jun. 13, 2023

(87) PCT Pub. No.: WO2022/132746

PCT Pub. Date: Jun. 23, 2022

(65) Prior Publication Data

US 2024/0041348 A1 Feb. 8, 2024

Related U.S. Application Data

(60) Provisional application No. 63/124,976, filed on Dec. 14, 2020.

(51) Int. Cl.
*A61B 5/103* (2006.01)
*A61B 5/00* (2006.01)

(52) U.S. Cl.
CPC ............ *A61B 5/1036* (2013.01); *A61B 5/002* (2013.01); *A61B 5/447* (2013.01);
(Continued)

(58) Field of Classification Search
CPC ...... A61B 2562/0247; A61B 2562/046; A61B 5/445; A61B 5/447; A61B 5/01;
(Continued)

(56) References Cited

U.S. PATENT DOCUMENTS 8,111,165 B2 2/2012 Ortega et al.
8,539,627 B2 9/2013 Terawaki et al.
(Continued)

FOREIGN PATENT DOCUMENTS

JP 5167409 B2 3/2013
WO WO2010119441 A2 * 10/2010

OTHER PUBLICATIONS

Search Report for EP 21907618.9 received Jul. 5, 2024; 8 pps.
International Search Report and Written Opinion issued for PCT/US2021/063277, dated Apr. 7, 2022 (8 pages).

*Primary Examiner* — Patrick Fernandes
*Assistant Examiner* — Shawn Curtis Broughton
(74) *Attorney, Agent, or Firm* — Armstrong Teasdale LLP

(57) ABSTRACT

A continuous bedside pressure monitoring (CBPM) device includes an array of pressure sensors, a controller including a processor and a memory, the controller operatively coupled to the array of pressure sensors, a communication interface operatively coupled to the controller, and a flexible housing enclosing the array of pressure sensors, the controller, and the communication interface.

18 Claims, 20 Drawing Sheets
(8 of 20 Drawing Sheet(s) Filed in Color)

(52) U.S. Cl.
CPC ................. *A61B 2560/0214* (2013.01); *A61B 2562/0247* (2013.01); *A61B 2562/046* (2013.01); *A61B 2562/166* (2013.01)

(58) Field of Classification Search
CPC .................. A61B 5/002; A61B 5/0008; A61B 2560/0412; A61B 2560/0214; A61B 5/6833; A61B 5/6823; A61B 5/1036; A61B 2562/166; G01L 1/205
See application file for complete search history.

(56) References Cited

U.S. PATENT DOCUMENTS

| | | | | |
|---|---|---|---|---|
| 10,588,565 | B2 | 3/2020 | Larson et al. | |
| 10,638,969 | B2 | 5/2020 | Drennan | |
| 2010/0100160 | A1 * | 4/2010 | Edman | A61B 5/444<br>607/88 |
| 2013/0019408 | A1 | 1/2013 | Jacofsky et al. | |
| 2017/0020438 | A1 * | 1/2017 | Wang | A61B 5/117 |
| 2019/0104982 | A1 * | 4/2019 | Dunn | A61B 5/7264 |
| 2020/0352501 | A1 * | 11/2020 | Hunt | A61F 13/0206 |
| 2021/0361225 | A1 * | 11/2021 | Dunn | G16H 50/20 |
| 2022/0395229 | A1 * | 12/2022 | Everett | A61B 5/01 |

* cited by examiner

DEVICES AND SYSTEMS FOR PREVENTING THE DEVELOPMENT OF PRESSURE ULCERS

CROSS-REFERENCE TO RELATED APPLICATIONS

This application is a US National Stage Entry of International Patent Application No. PCT/US2021/063277 filed on Dec. 14, 2021, which claims priority to U.S. Provisional Patent Application Ser. No. 63/124,976 filed Dec. 14, 2020, the entire contents of which are hereby incorporated by reference in their entireties.

FIELD OF THE DISCLOSURE

The present disclosure generally relates to devices and systems for continuous monitoring of tissue pressures.

BACKGROUND OF THE DISCLOSURE

Pressure injuries are a pervasive and debilitating reality for over 2.5 million hospitalized and critically ill patients annually. Deemed a "never event" by the Center for Medicare & Medicaid Services (CMS), new pressure injuries in post-operative patients are estimated around 12-66%, while 10-41% of critically ill patients may suffer pressure sores. Individuals who develop pressure injuries are more likely to suffer mortality, with 60,000 deaths attributed directly to these wounds annually.

Compounding the morbidity and mortality suffered by patients who develop these wounds, their prevention has become even more vital in hospital settings as the reimbursement landscape, influenced by CMS, for hospital-acquired injuries changes. In 2008, CMS revised its Inpatient Prospective Payment System to reduce reimbursements for hospital stays associated with several hospital-acquired conditions including pressure injuries, thus placing the economic burden of prevention and treatment on hospitals and providers. These CMS policies have burdened hospital nursing staff to initiate best practice guidelines that prevent pressure ulcers.

While nursing providers, physicians, hospital administrators, and insurance providers are grappling with ways to prevent these injuries, the armamentarium for their prevention is decidedly limited. To date, the primary intervention available in the fight against pressure injury formation is manual repositioning of patients on a two-hour scheduled interval, a nationwide protocol that is not supported by clinical evidence. While this standardized approach integrates well into the daily nursing workflow, it does not account for differences in patient body habitus, illness, ability to shift position, and ability of a patient to sense painful pressures secondary to ischemia.

Various systems have been developed to monitor pressure experienced by the body of a patient. At least some such systems are prohibitively expensive and require replacement of patients' beds with special pressure sensing beds. Some other known systems only monitor pressure exceeding a threshold pressure, or monitor with limited sensors and/or accuracy.

Other objects and features will be in part apparent and in part pointed out hereinafter.

SUMMARY

One aspect of this disclosure is a continuous bedside pressure monitoring (CBPM) device including an array of pressure sensors, a controller including a processor and a memory, the controller operatively coupled to the array of pressure sensors, a communication interface operatively coupled to the controller, and a flexible housing enclosing the array of pressure sensors, the controller, and the communication interface.

Various refinements exist of the features noted in relation to the above-mentioned aspect. Further features may also be incorporated in the above-mentioned aspect as well. These refinements and additional features may exist individually or in any combination. For instance, various features discussed below in relation to any of the illustrated embodiments may be incorporated into the above-described aspect, alone or in any combination.

DESCRIPTION OF THE DRAWINGS

The patent or application file contains at least one drawing executed in color. Copies of this patent or patent application publication with color drawing(s) will be provided by the Office upon request and payment of the necessary fee.

Those of skill in the art will understand that the drawings, described below, are for illustrative purposes only. The drawings are not intended to limit the scope of the present teachings in any way.

Figure 1:
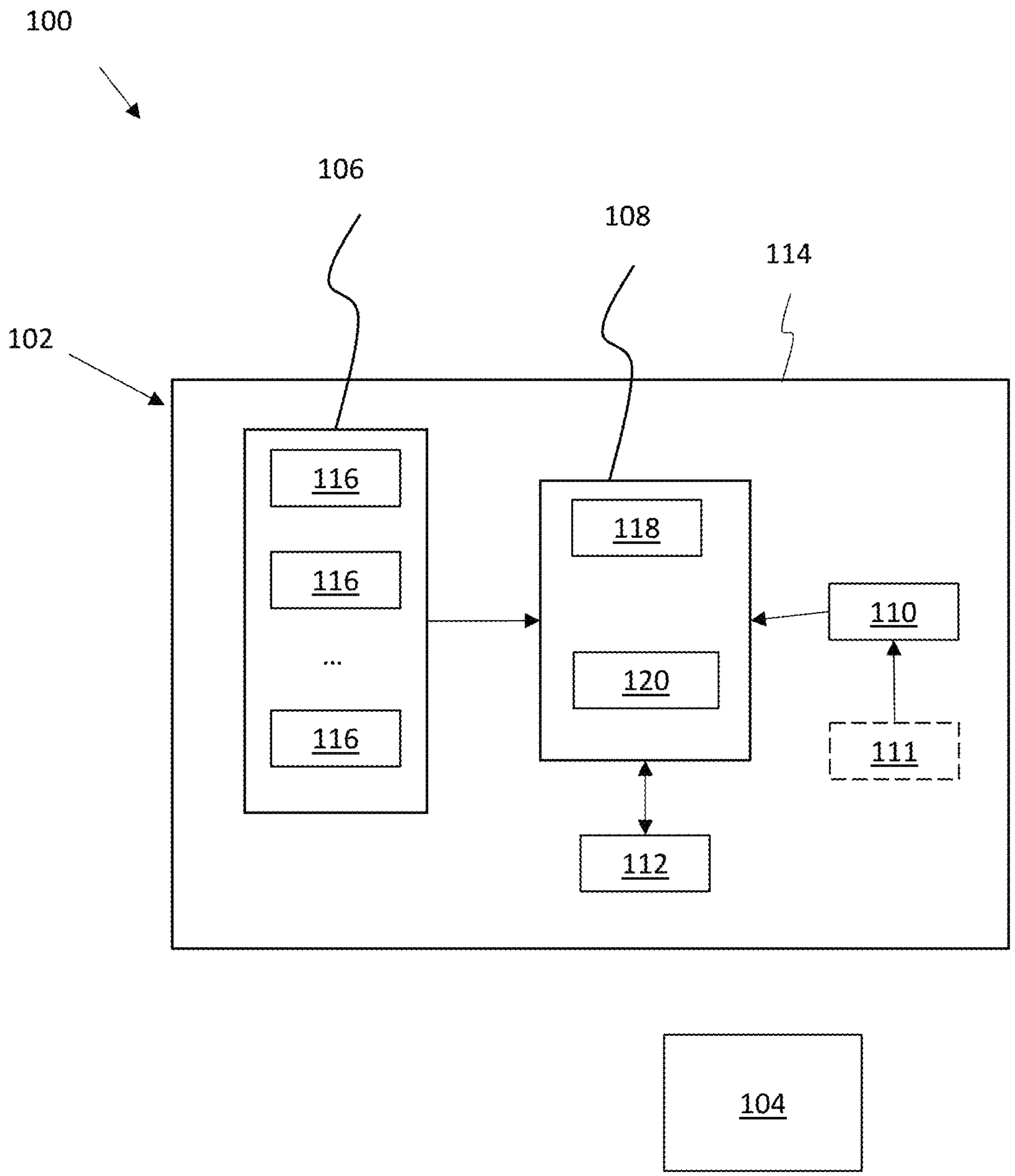
FIG. 1 is a block diagram of a continuous bedside pressure monitoring (CBPM) system in accordance with one aspect of the disclosure.

There are shown in the drawings arrangements that are presently discussed, it being understood, however, that the present embodiments are not limited to the precise arrangements and are instrumentalities shown. While multiple embodiments are disclosed, still other embodiments of the present disclosure will become apparent to those skilled in the art from the following detailed description, which shows and describes illustrative aspects of the disclosure. As will be realized, the invention is capable of modifications in various aspects, all without departing from the spirit and scope of the present disclosure. Accordingly, the drawings and detailed description are to be regarded as illustrative in nature and not restrictive.

DETAILED DESCRIPTION

In various aspects, continuous bedside pressure monitoring (CBPM) devices and systems for performing continuous bedside pressure monitoring and thereby preventing the development of pressure ulcers are disclosed.

In some aspects, the CBPM device is a single-use thin, wireless, flexible array of pressure sensors which is positioned in conjunction with normal foam border dressings at the anatomical location at risk for development of a pressure ulcer (e.g., the sacrum, hip, heel, occiput, etc.). The CBPM device may include a battery, flexible printed circuit board, Bluetooth communication module, and an array of force sensing elements to detect pressure, all completely housed within a water-resistant, sealed soft EcoTec overmold housing Once placed over the anatomical area of concern, the CBPM device continually monitors any pressures experienced within the array of force sensors, calculates the cumulative "dose" of pressure being received at the anatomical site, and wirelessly communicates the collected information to an external monitoring device or EDC/EMR system. The external monitoring device or EDC/EMR system then alerts appropriate clinicians and/or nursing staff to intervene and offload the anatomical location/patient in the event that an injurious instantaneous pressure level or cumulative "dose" of pressure is experienced by the patient. In various aspects, the CBPM device and associated system enable the prevention and progression of pressure ulcers across multiple anatomical locations and clinical settings. The devices and systems described provide a means of continuous pressure sensing that may be easily and safely placed on one or more pressure points of a patient. Based on an analysis of the pressures obtained using the disclosed devices, the system may wirelessly alert providers to critical patient pressures associated with ischemia and pressure injury formation.

In various aspects, the disclosed CBPM devices and systems aim to change the clinical practice algorithm for the prevention of pressure injuries with the aid of a proprietary single-use device and system capable of detecting patients/anatomical locations at high risk of developing pressure ulcers and alerting clinicians/nursing staff to intervene prior to pressure ulcer development. The disclosed CBPM devices and systems provide for more effective clinical practice algorithms to prevent pressure injuries. The disclosed CBPM device has the capability of dramatically changing practice paradigms, as the antiquated system of scheduled patient turning is supplanted with a cost-effective device relaying individualized patient data to inform an evidence-based offloading schedule. While patient turning on standardized time intervals is currently the standard of care, these existing protocols may be upgraded to incorporate evidence-based patient offloading. Using patient pressures monitored using the disclosed CBPM devices and systems, patient turning based on detected critical pressure levels may reduce pressure sore incidence. Use of the disclosed CBPM devices and systems, integrated with novel clinical algorithms, could bring the incidence of pressure injuries closer to 0% and truly make these preventable injuries a "never event".

The disclosed CBPM device overcomes at least some of the limitations of existing devices and systems. Existing products fail to offer pressure point specific pressure readings in a cost-effective manner and also provide evidence-based recommendations when turning should occur. Two known systems include the Leaf System (Leaf Healthcare, Pleasanton, USA) and the CONFORMat (Tekscan, Boston, USA). Leaf Healthcare has created the wireless Leaf Patient Monitoring System, a wearable patient sensor that monitors patient movement. It interfaces wirelessly with a tablet and highlights patients who have not been turned or moved for prolonged periods of time. However, while research has shown that the Leaf increases compliance with standardized patient turning protocols, it does not measure pressure or incorporate individualized patient characteristics into its alerts. The CONFORMat is a Body Pressure Measurement System that allows identification of full-body pressures. While this state-of-the-art pressure mapping system accurately details pressure, this system does not provide an evidence-based model for high pressures associated with pressure sore formation. Further, this system is also prohibitively expensive, making the CONFORMat impractical for large-scale hospital use.

FIG. 1 is a block diagram of an example CBPM system 100 according to the present disclosure. The CBPM system includes a CBPM device 102 (sometimes referred to as a CBPM patch) and a monitoring device 104. In use, the CBPM device is positioned on body of a patient and communicatively coupled to the monitoring device. The CBPM device monitors the pressure experienced by the patient at the location of the CBPM device and reports the monitored pressure to the monitoring device. In the example embodiment, the CBPM device monitors the pressure and reports the monitored pressure continuously or substantially continuously. That is, as pressure is monitored, the pressure is reported to the monitoring device, rather than accumulating data and then reporting it, only checking the pressures periodically, or only reporting pressures when they exceed a threshold. Even continuous monitoring may be practically limited by the sampling rate, the number of pressure sensors included in the CBPM device, the time required to acquire, process, and transmit signals from the pressure sensors, and the like. As used herein, continuously monitoring and reporting pressures includes sensing pressure continuously subject to such physical and practical limitations. In some embodiments, the CBPM device monitors the pressure continuously, but only reports the monitored pressures intermittently. The time between reports may be a predetermined length of time, such as every thirty seconds, every minute, every five minutes, and the like, or may be based on the number of measurements of pressure acquired, such as after every five measurements, every ten measurements, or the like.

The CBPM device 102 includes a sensor array 106, a controller 108, a power source 110, a charging interface 111 (optional), and a communication interface 112. The sensor array, controller, and communications interface are mounted on a flexible circuit board (not shown in FIG. 1). A flexible housing 114 encloses the sensor array, controller, communications interface, and battery.

The sensor array 106 includes multiple pressure sensors 116. The pressure sensors may be any type of sensor operable to sense the amount of pressure applied to the sensor. The number of pressure sensors may vary depending on the size of the CBPM device 102, the area of the patient's body to be monitored, and the size of the other components in the CBPM device. In some embodiments, the sensor array includes seven pressure sensors.

The controller 108 is operatively connected to the pressure sensors 116 of the sensor array 106. The controller includes a processor 118 and a memory 120. The memory stores instructions that, when executed by the processor, configure the processor to perform as described herein. Although illustrated as separate components, the memory and the processor may be part of an integrated controller, such as in a microcontroller. The processor may include one or more processing units (e.g., in a multi-core configuration) . The term processor, as used herein, refers to central processing units, microprocessors, microcontrollers, reduced instruction set circuits (RISC), application specific integrated circuits (ASIC), a programmable logic circuit (PLC), and any other circuit or processor capable of executing the functions described herein. The above are examples only, and are thus not intended to limit in any way the definition and/or meaning of the term "processor." The memory stores non-transitory, computer-readable instructions for performance of the techniques described herein. Such instructions, when executed by the processor, cause the processor to perform at least a portion of the methods described herein. The memory may include, but is not limited to, random access memory (RAM) such as dynamic RAM (DRAM) or static RAM (SRAM), read-only memory (ROM), erasable programmable read-only memory (EPROM), electrically erasable programmable read-only memory (EEPROM), and non-volatile RAM (NVRAM). The above memory types are examples only, and are thus not limiting as to the types of memory usable for storage of a computer program.

The communication interface 112 is operatively coupled to the controller 108 and enables the controller to communicate with remote devices, such as the monitoring device 104. The communication interface may include more than one communication interface for interacting with more than one remote device or system. In the example embodiment, the communication interface is a wireless communication interface, but the communication interface may be a wired communication interface in other embodiments. The communication interface may be any wired or wireless communications interface that permits the controller to communicate with the monitoring device or other the remote devices and systems directly or via a network. Wireless communication interfaces may include a radio frequency (RF) transceiver, a Bluetooth® adapter, a Wi-Fi transceiver, a ZigBee® transceiver, a near field communication (NFC) transceiver, an infrared (IR) transceiver, and/or any other device and communication protocol for wireless communication. (Bluetooth is a registered trademark of Bluetooth Special Interest Group of Kirkland, Washington; ZigBee is a registered trademark of the ZigBee Alliance of San Ramon, California.) Wired communication interfaces may use any suitable wired communication protocol for direct communication including, without limitation, USB, RS232, I2C, SPI, analog, and proprietary I/O protocols. In some embodiments, the wired communication interfaces include a wired network adapter allowing the computing device 400 to be coupled to a network, such as the Internet, a local area network (LAN), a wide area network (WAN), a mesh network, and/or any other network to communicate with remote devices and systems via the network.

In the example embodiment, the power source 110 is a battery. The battery may be any suitable type of rechargeable or single-use battery having any suitable battery chemistry. In some embodiments, the power source is a lithium based rechargeable battery. Moreover, the power source 110 may include more than one battery connected in series, parallel, or a combination of series and parallel in order to meet the desired voltage and/or capacity requirements for the CBPM device 102. In other embodiments, any other suitable power source may be used, including wireless energy receivers, photovoltaic cells, energy harvesters, a connector for connection to an external power source, or the like. The charging interface 111 is generally included in embodiments in which the power source is a rechargeable battery. The charging interface receives energy from an external power source and uses it to charge the rechargeable battery. The charging interface includes suitable charge control circuitry in some embodiments. In some embodiments, the charging interface is a wireless charging interface for wirelessly receiving energy to charge the power source. Other embodiments include a wired charging interface.

The flexible housing 114 encloses the sensor array 106, the controller 108, the power source 110, the communication interface 112, and (when included) the charging interface 111. In the example embodiment, the flexible housing is a sealed, waterproof, flexible housing. The flexible housing is flexible to allow the CBPM device 102 to conform to the shape of different body locations and to allow the CBPM device to move with the body to which it is attached. The flexible housing may be made of any flexible material suitable for use in contact with a patient's body. In some embodiments, the flexible housing may include an appropriate adhesive on one surface of the housing for attaching the CBPM device to a patient's body.

Figure 2:
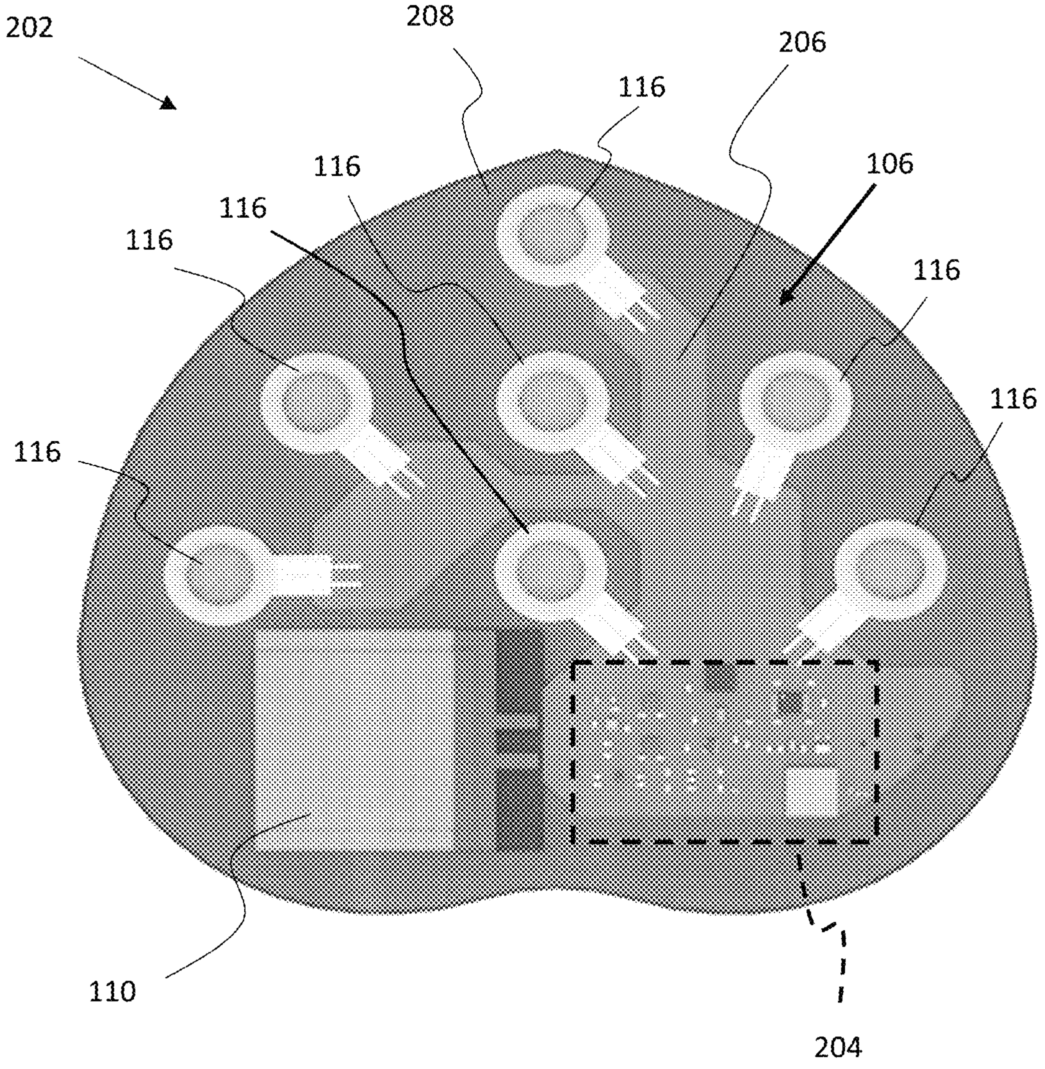
FIG. 2 is a plan view of an example CBPM device for use in the CBPM system of FIG. 1, with a top layer of its packaging removed.

FIG. 2 is a plan view of an example CBPM device 202 for use as the CBPM device 102 in the CBPM system 100 of FIG. 1, with a top layer of its packaging removed. In this example, the CBPM device is a wireless, heart-shaped, and flexible device. In this example, the power source 110 is a battery, and the sensor array 106 includes seven pressure sensors 116. The pressure sensors are force-sensitive resistor (FSR) elements to detect pressure. The controller 108 and the communication interface 112 are part of the circuitry 204 mounted on a flexible circuit board 206 (also referred to as a flexible printed circuit board (PCB)). The battery, sensor array, flexible circuit board, and circuitry are all housed in a water-resistant, sealed silicone overmold as the flexible housing 114. A bottom layer 208 of the flexible housing 114 is visible, but the top layer is removed in FIG. 2 to allow the internal components to be viewed. In some aspects, the CBPM device includes a custom FSR array overmolded in a Shore 10A RTV silicone housing, providing flexibility and pressure detection sensitivity.

Figure 3:
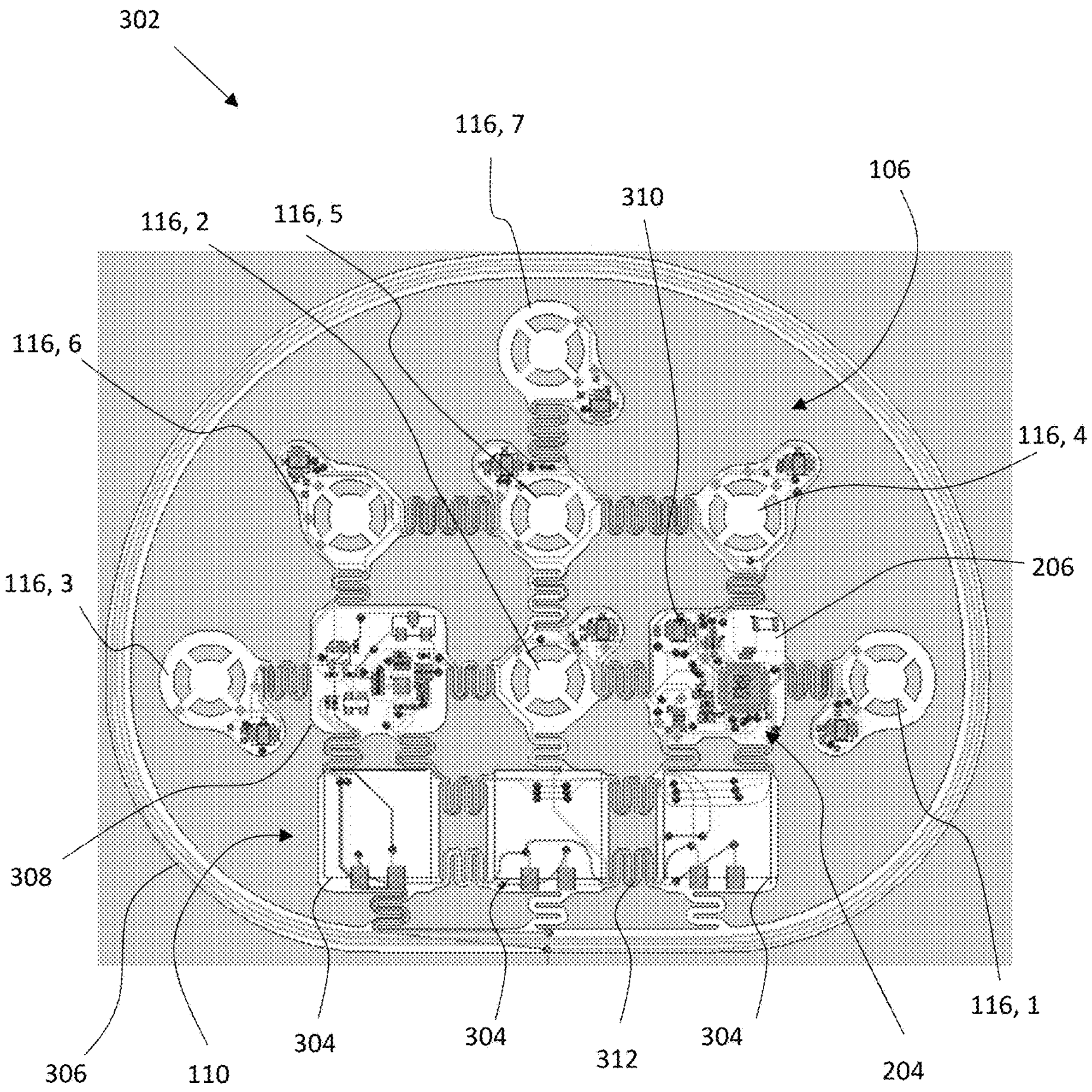
FIG. 3 is a diagram of the electrical components of another example CBPM device.
Figure 4:
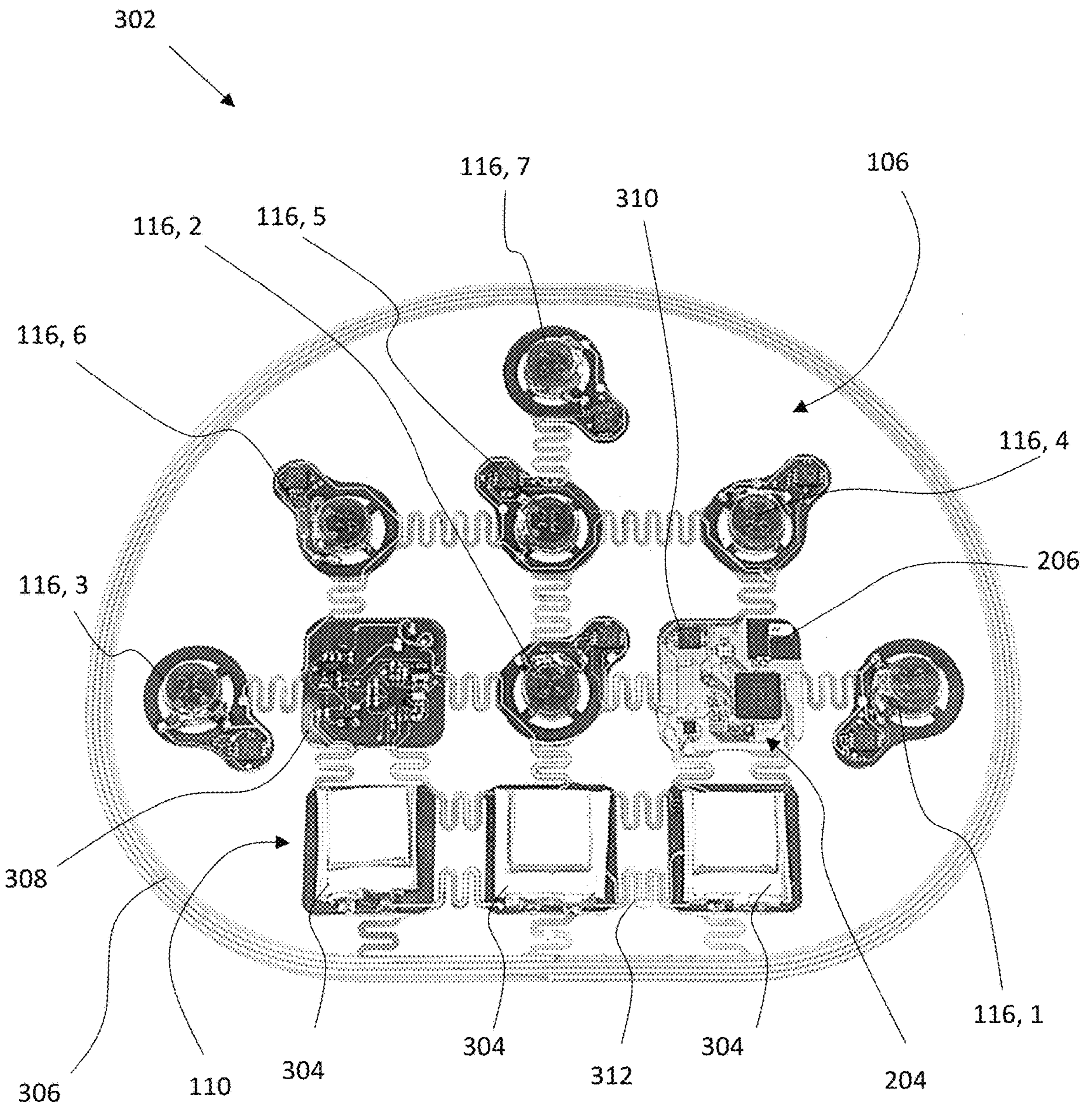
FIG. 4 is a photograph of a CBPM device according to the diagram illustrated in FIG. 3.
Figure 20:
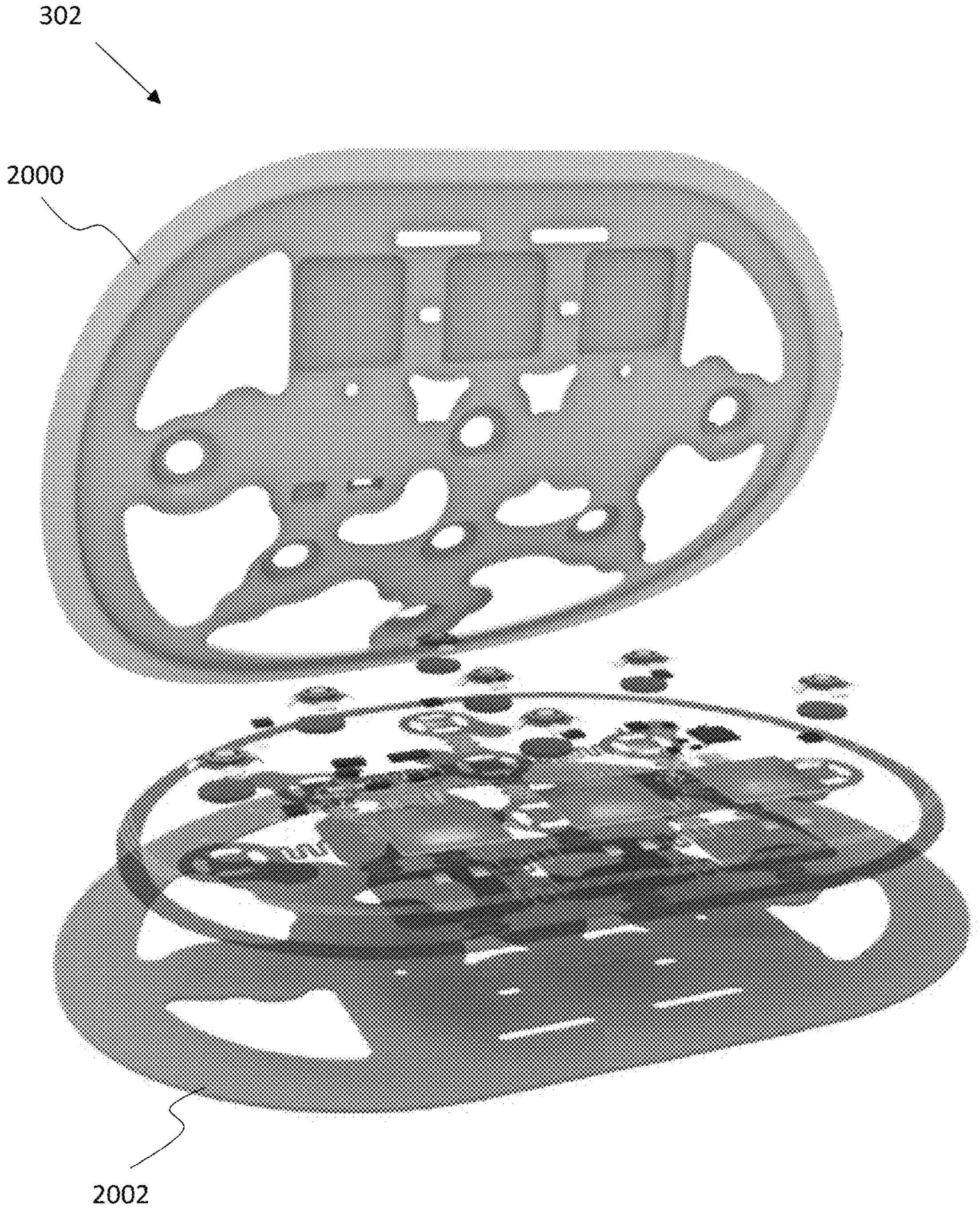
FIG. 20 is an exploded view of the CBPM device of FIG. 4.

FIG. 3 is a diagram of the electrical components of another example CBPM device 302 usable as the CBPM device 102 in the CBPM system 100, and FIG. 4 is a photograph of a CBPM device 302 according to the diagram illustrated in FIG. 3. FIG. 20 is an exploded view of the CBPM device 302. The flexible housing 114 is removed in FIGS. 3 and 4, but is visible as an upper housing 2000 and a lower housing 2002 in FIG. 20. In these examples, the power source 110 includes three batteries 304 electrically connected together in parallel. The batteries are DNK201515 batteries, each of which has a capacity of 20 milliamp hours (mAh). Thus, the parallel connection of the batteries provides a power source with a capacity of 60 mAh. The sensor array 106 includes seven pressure sensors 116. For ease of reference to specific sensors 116, the sensors are also referenced by reference numerals 1-7. The pressure sensors are force-sensitive resistor (FSR) elements to detect pressure. In this example, the charging interface 111 (not numbered in FIG. 3) includes planar coils 306 and wireless charging controller 308 for wirelessly charging batteries 304. The circuitry 204 includes the communication interface 112, the controller 108, and a temperature sensor 310 on flexible circuit board 206. The conductive traces 312 between components (and their underlying flexible circuit board) are serpentine shaped to increase the flexibility of the CBPM device.

Figure 6:
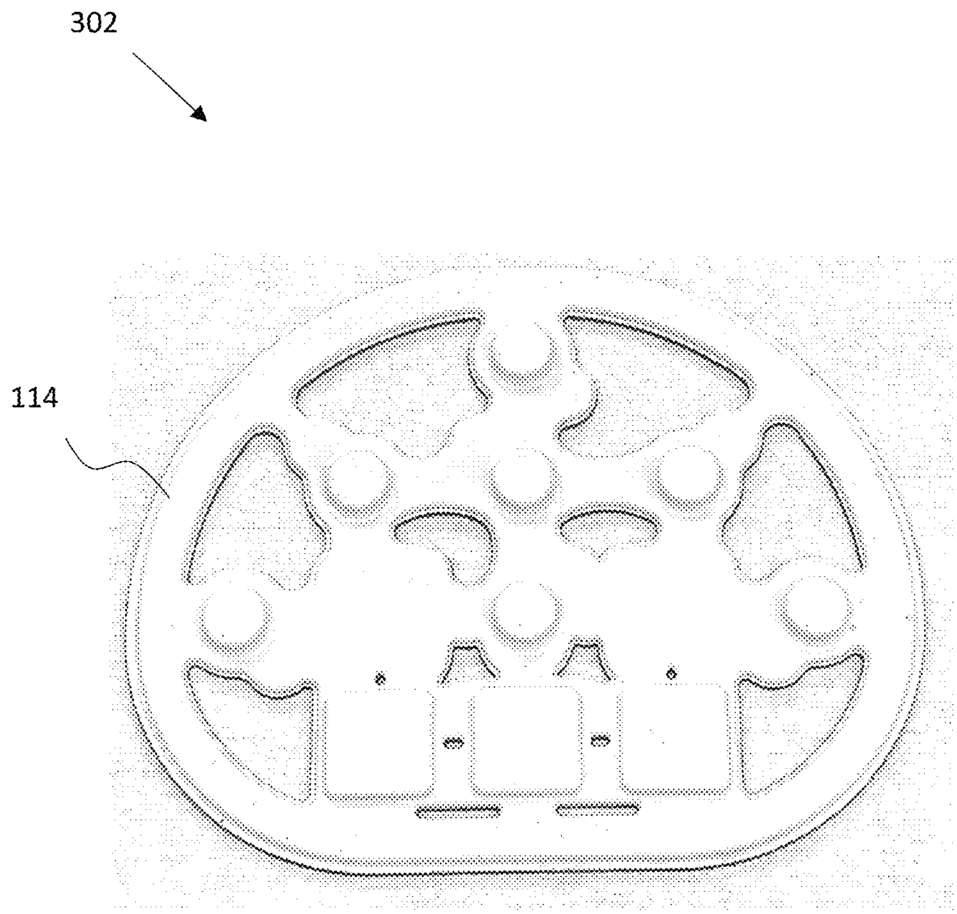
FIG. 6 is a front-view image of the CBPM device shown in FIG. 4 enclosed in a water-resistant flexible packaging.
Figure 7:
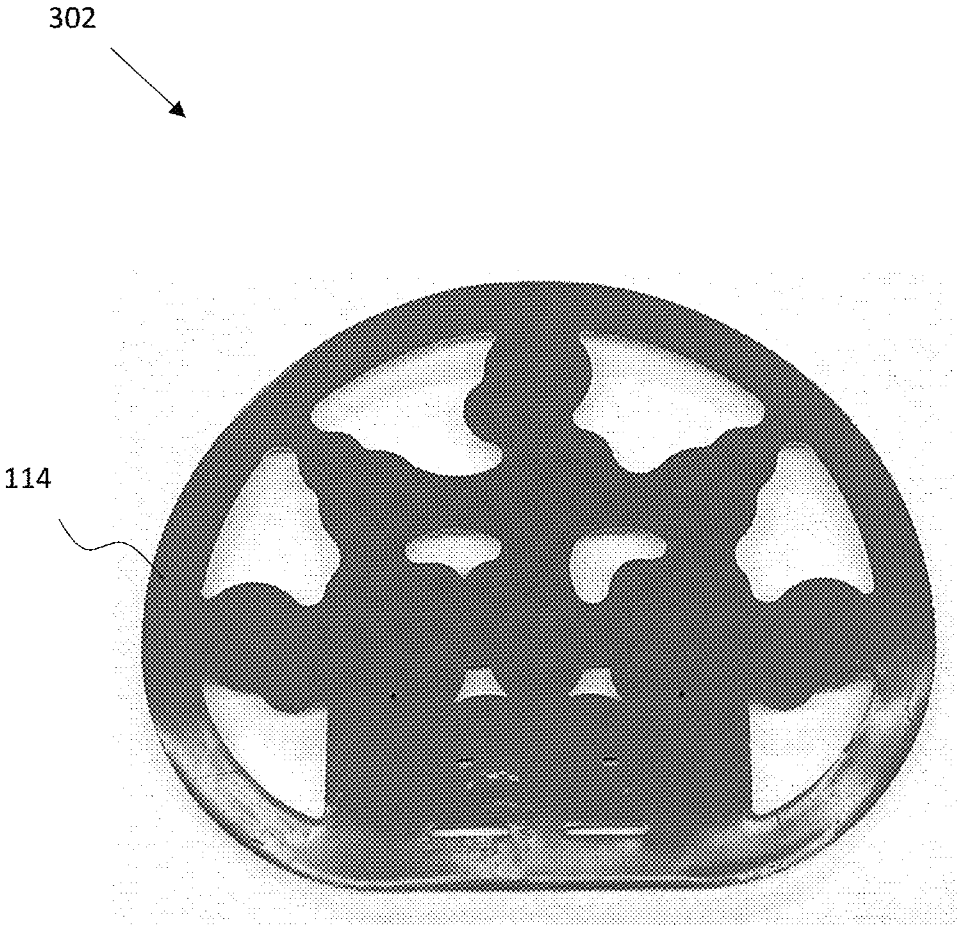
FIG. 7 is a back-view image of the CBPM device shown in FIG. 4 enclosed in the water-resistant flexible packaging of FIG. 6.
Figure 8A:
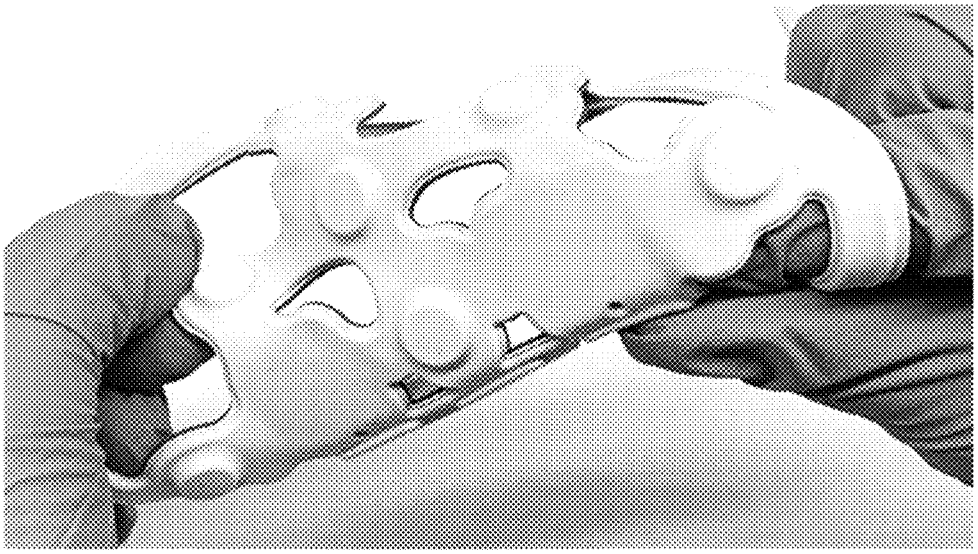
FIG. 8A is an image of the CBPM device of FIGS. 6 and 7 during twisting.
Figure 8B:
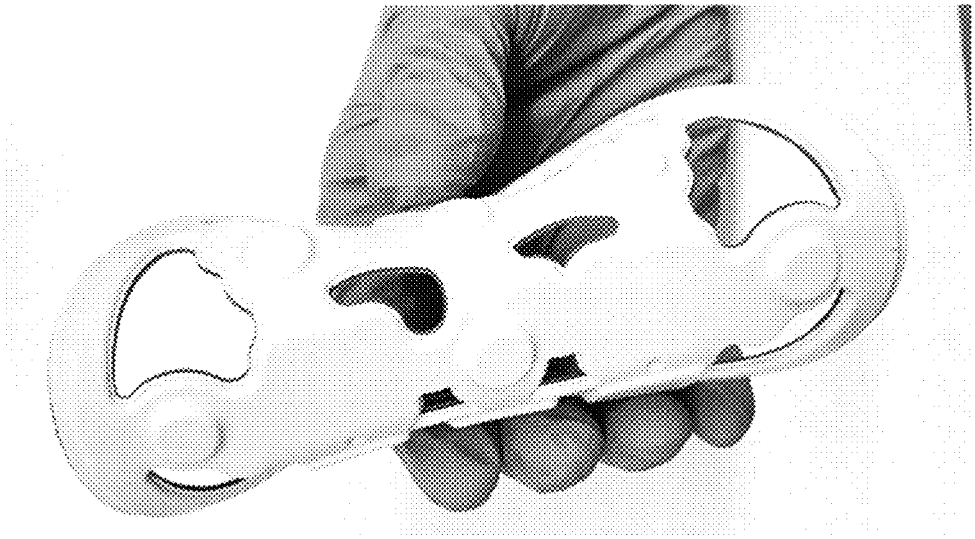
FIG. 8B is an image of the CBPM device of FIGS. 6 and 7 during horizontal bending.
Figure 8C:
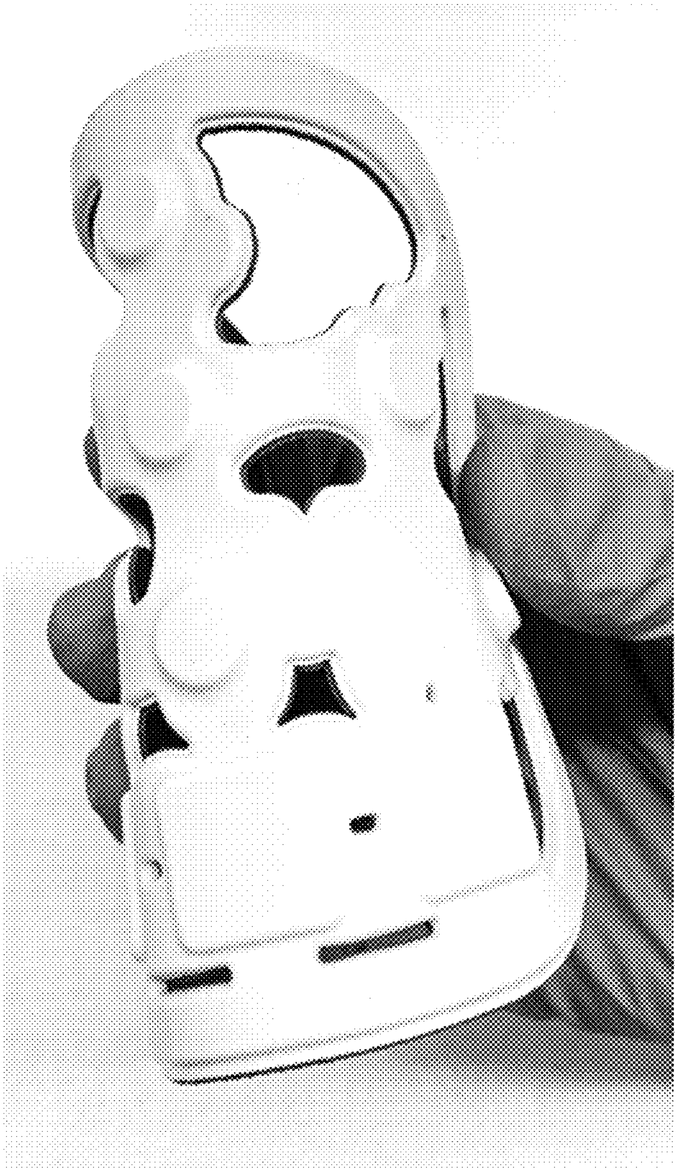
FIG. 8C is an image of the CBPM device of FIGS. 6 and 7 during horizontal bending about an axis parallel with the corresponding axis of FIG. 8B.

FIG. 6 is a front-view image of the CBPM device 302 shown in FIG. 4 enclosed in flexible housing 114, which is a water-resistant flexible packaging. FIG. 7 is a back-view image of the CBPM device 302 enclosed in the flexible housing. FIG. 8A is an image of the CBPM device 302 of FIGS. 6 and 7 during twisting. FIG. 8B is an image of the CBPM device 302 during horizontal bending. FIG. 8C is an image of the CBPM device 302 during horizontal bending about an axis parallel with the corresponding axis of FIG. 8B.

Figure 9:
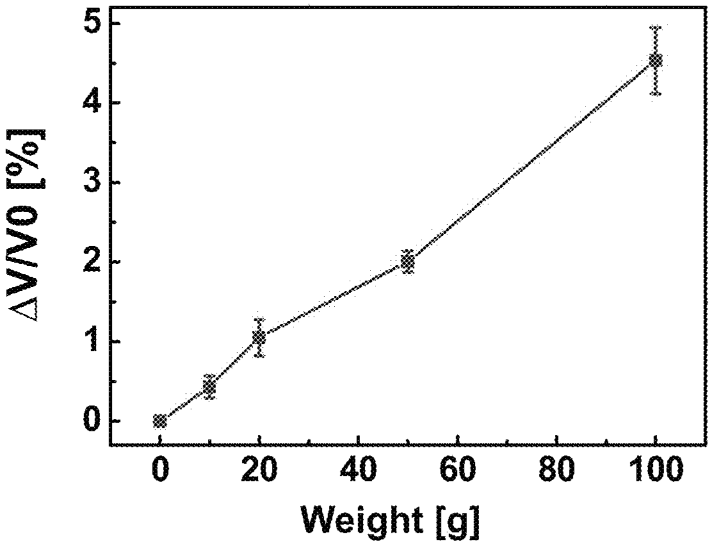
FIG. 9 is a graph summarizing the readouts from a single pressure sensor of the CBPM device of FIG. 4 for a range of loadings.
Figure 10:
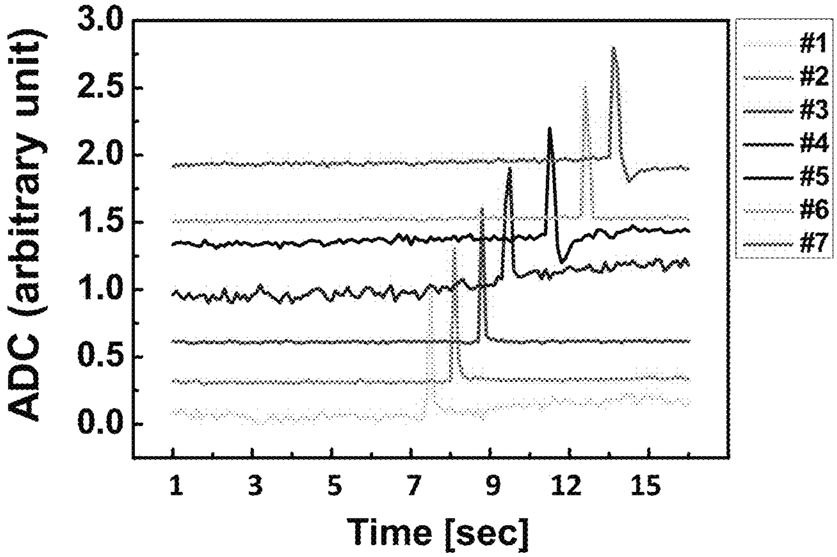
FIG. 10 is a graph illustrating the outputs of the individual pressure sensors of the CBPM device of FIG. 4 when each is pressed at a different time.
Figure 11:
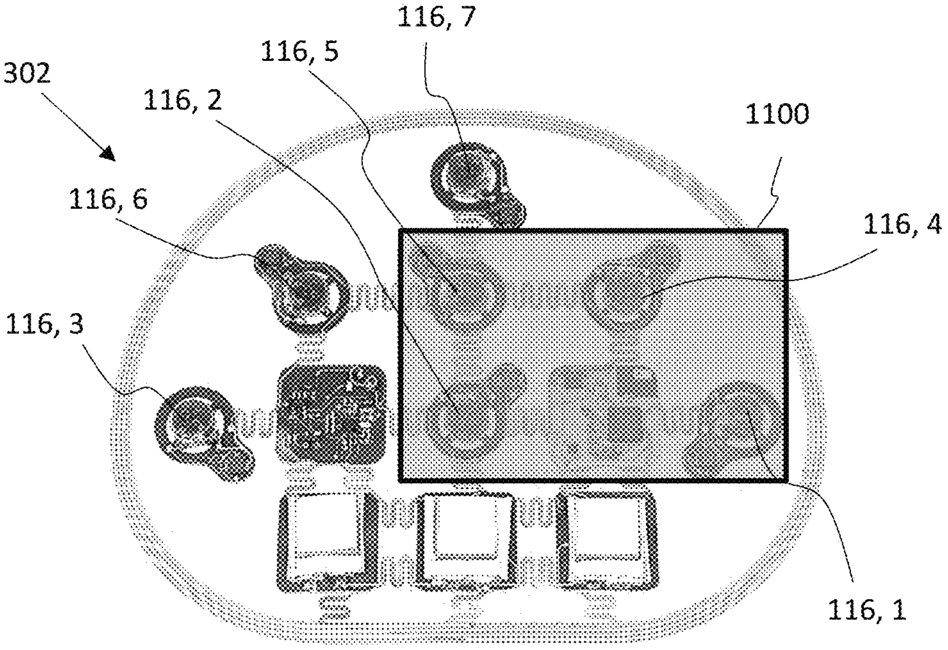
FIG. 11 is a view of the CBPM device of FIG. 4 with a plate positioned on top of a first group of the sensors of the CBPM device.
Figure 12:
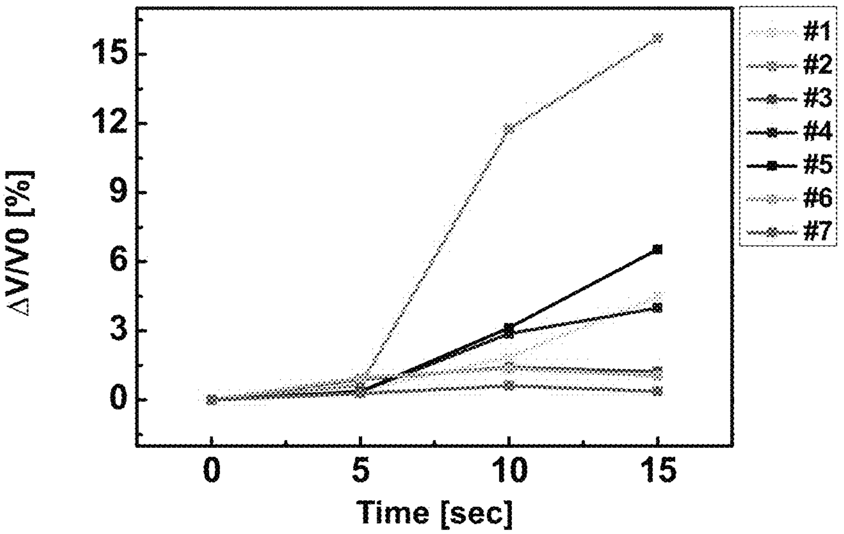
FIG. 12 is a graph illustrating the outputs of individual pressure sensors of the CBPM device with the plate positioned as shown in FIG. 11.
Figure 13:
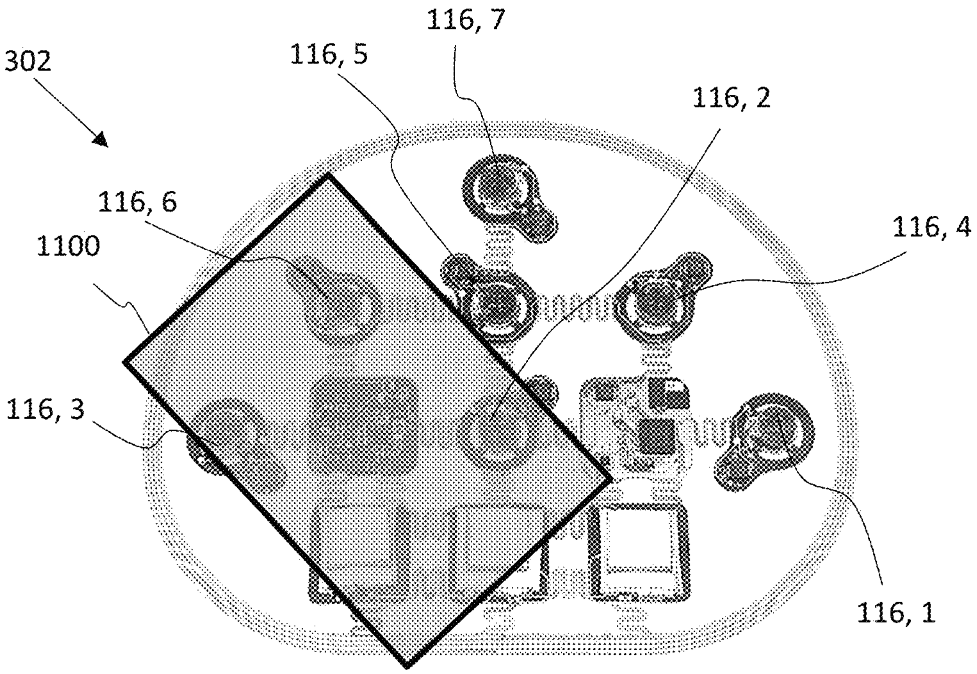
FIG. 13 is a view of the CBPM device of FIG. 4 with a plate positioned on top of a second group of the sensors of the CBPM device.
Figure 14:
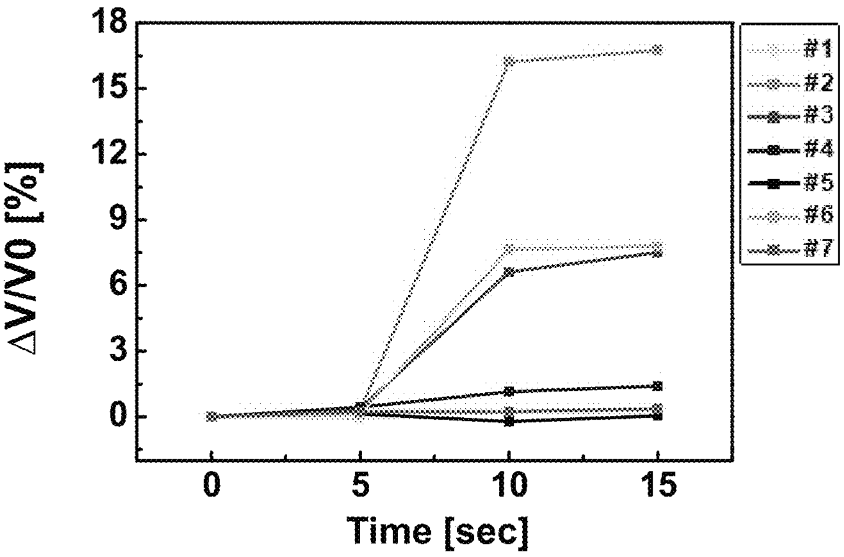
FIG. 14 is a graph illustrating the outputs of individual pressure sensors of the CBPM device with the plate positioned as shown in FIG. 13.
Figure 17A:
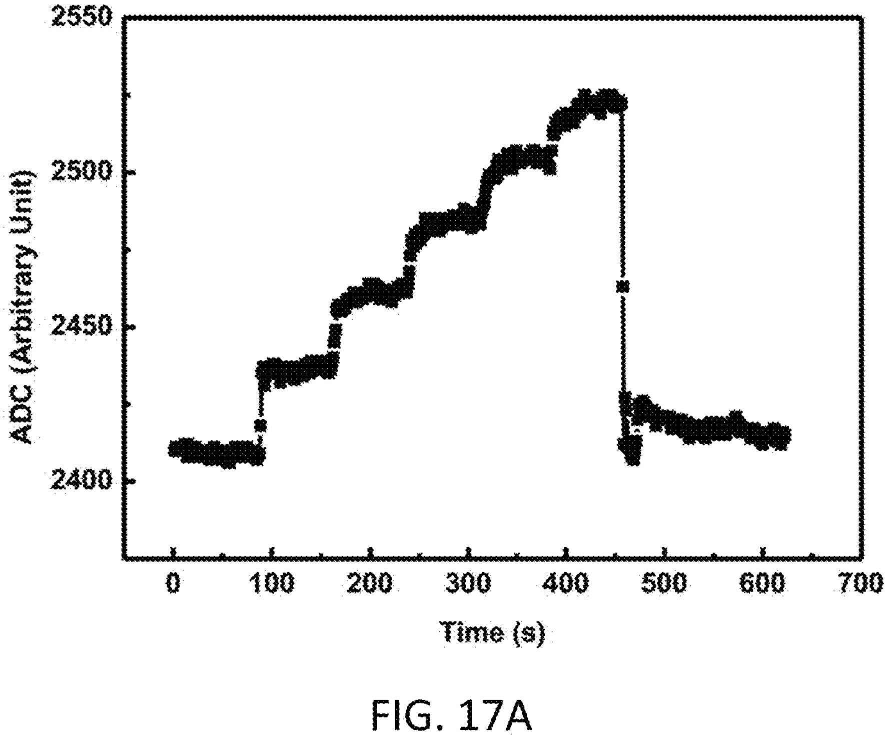
FIG. 17A is a graph of a step-wise pressure sensing by the CBPM device of FIG. 4 as a function of time.
Figure 17B:
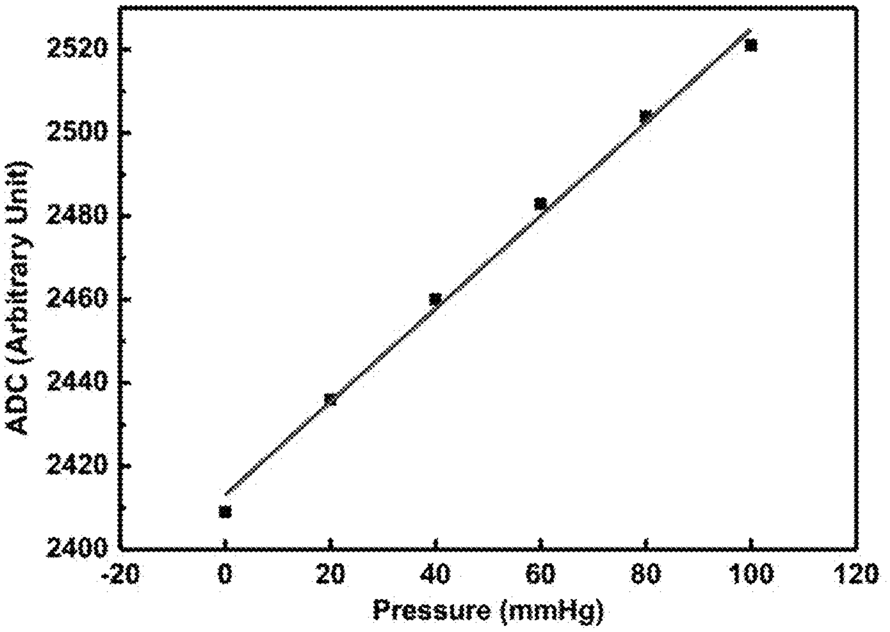
FIG. 17.B is a graph of the sensed pressures of FIG. 17A.

FIG. 9 is a graph summarizing the readouts from a single pressure sensor 116 of the CBPM device 302 of FIG. 4 for a range of loadings. FIG. 10 is a graph illustrating the outputs of the individual pressure sensors 116 (1-7) of the CBPM device 302 of FIG. 4 when each is pressed at a different time. FIG. 11 is a view of the CBPM device 302 with a plate 1100 positioned on top of a first group of the sensors 316 of the CBPM device. FIG. 12 is a graph illustrating the outputs of the individual pressure sensors 116 of the CBPM device with the plate positioned as shown in FIG. 11. FIG. 13 is a view of the CBPM device 302 with the plate 1100 positioned on top of a second group of the sensors 116 of the CBPM device. FIG. 14 is a graph illustrating the outputs of individual pressure sensors of the CBPM device with the plate positioned as shown in FIG. 13. FIG. 17A is a graph of a step-wise pressure sensing by the CBPM device 302 of FIG. 4 as a function of time, and FIG. 17.B is a graph of the sensed pressures of FIG. 17A.

Figure 18A:
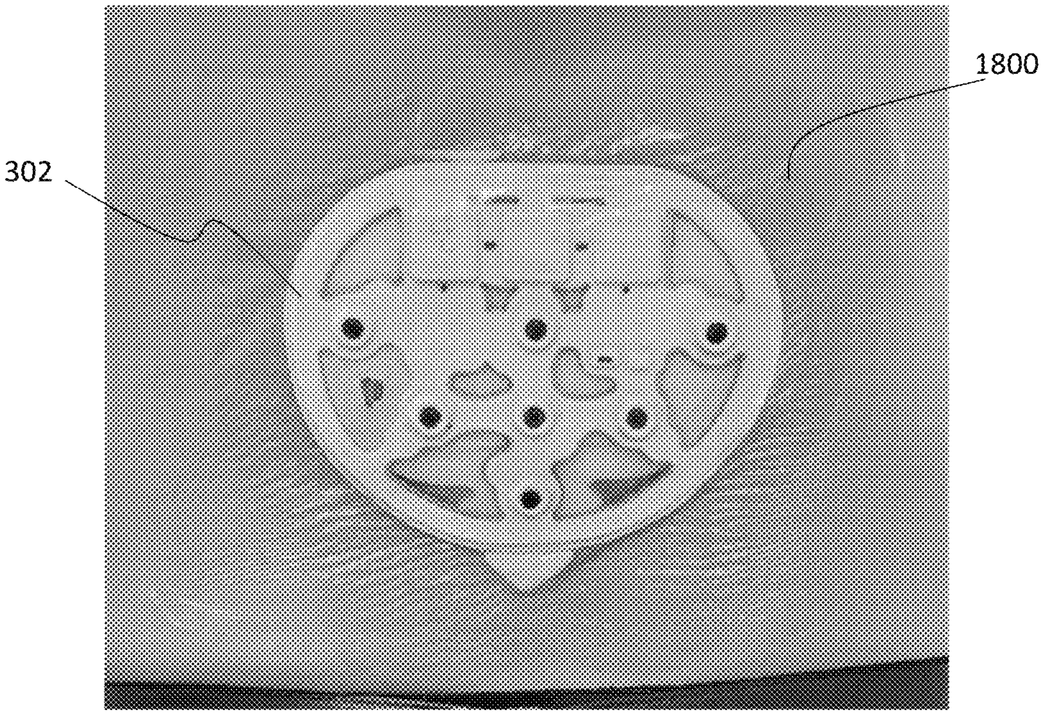
FIG. 18A is an image of the CBPM device of FIG. 4 positioned on the back of a patient.
Figure 18B:
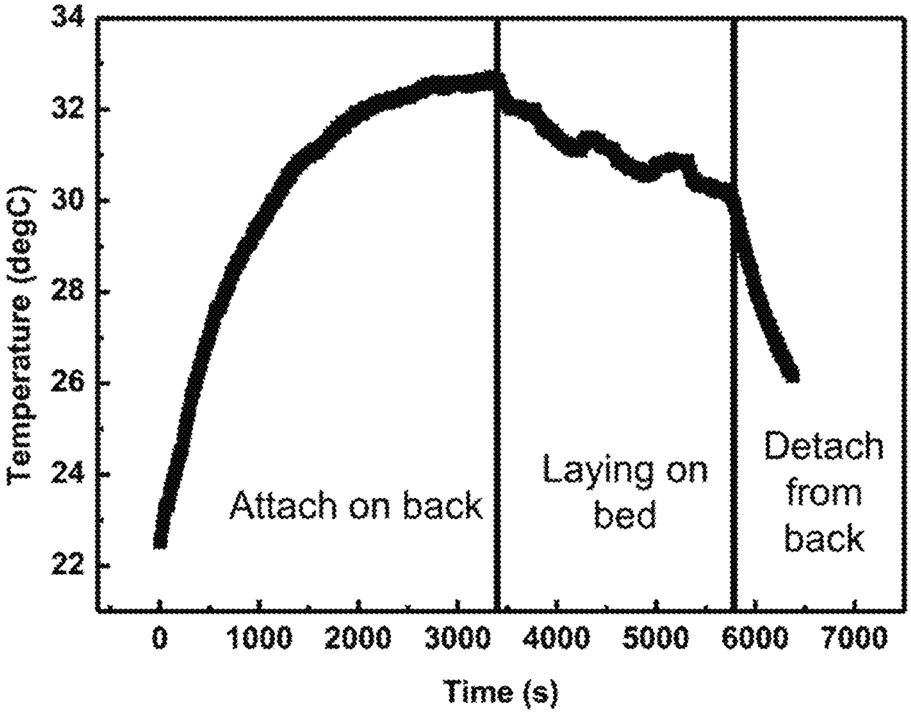
FIG. 18B is a graph of the measured temperature during positioning, wearing, and removal of the CBPM as shown in FIG. 18A.
Figure 18C:
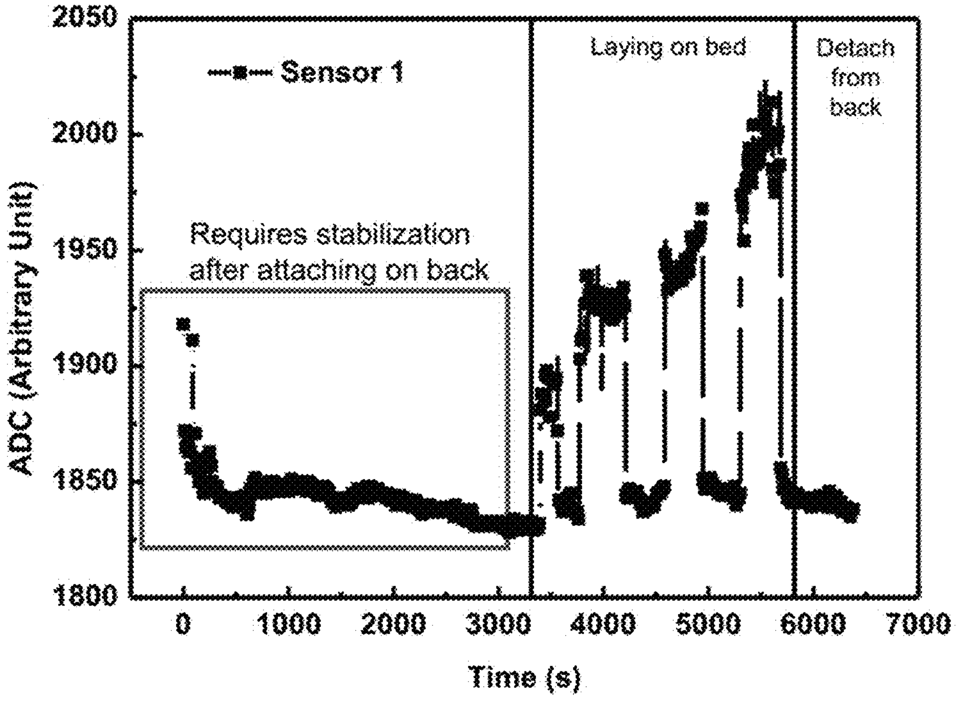
FIG. 18C is a graph of the pressure sensor output during positioning, wearing, and removal of the CBPM as shown in FIG. 18A.
Figure 19:
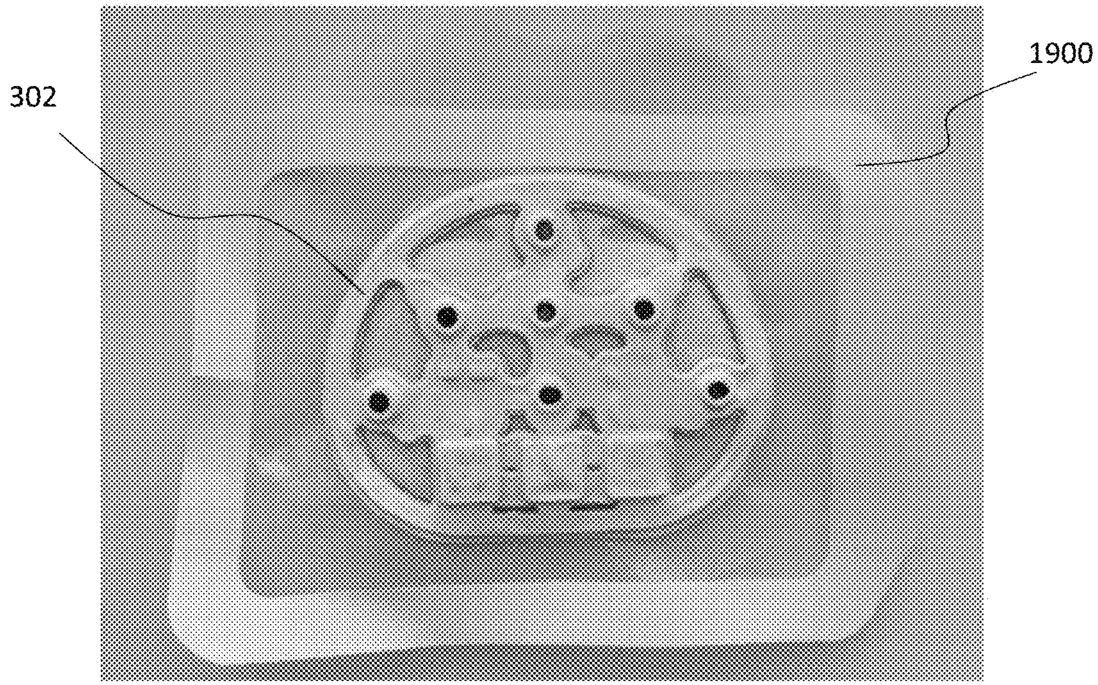
FIG. 19 is an image of the of the CBPM device of FIG. 4 attached to a bandage in preparation for attachment to a patient.

The CBPM device 102, 202, 302 is configured to sit comfortably outside an absorbent foam boarder dressing that overlays pressure points. In some aspects, the CBPM is primarily constructed using flexible materials including, but not limited to, silicone. FIG. 19 is an image of the CBPM device assembled with a bandage 1900 for attachment to the body of a patient. FIG. 18A is a photograph of the CBPM device 302 attached to the back of a patient using a different bandage configuration 1800. FIG. 18B is a graph of the temperature measured by the CBPM device 302 over time as the bandage is attached to the back of the patient in FIG. 18A, as the patient lies on the bed with the attached CBPM device 302, and as the bandage is detached from the patient. FIG. 18C is a graph of the pressure measured by the CBPM device 302 over time as the bandage is attached to the back of the patient in FIG. 18A, as the patient lies on the bed with the attached CBPM device 302, and as the bandage is detached from the patient.

The CBPM device 102, 202, 302 is designed to detect pressures between 0-400 mmHg, within a 10 mmHg margin of error. In some aspects, all electronics (e.g., controller 108, communication interface 112, conductive traces, etc.) are consolidated into a single four-layer flexible printed circuit board (PCB board) 206 located within the silicone monitoring layer. This PCB circuit board provides for the mounting and electronic coupling of a variety of electrical components. In this example, the controller 108 is an Arm Cortex-M4F processor with a multi-channel analog to digital converter system (ADC) and general-purpose input/outputs (GPIOs) for standalone control. In this example, the power source 110 is a rechargeable battery positioned within the silicone housing. Non-limiting examples of suitable batteries include at least one PowerStream 3.7v, 35 mAh ultrathin rechargeable lithium polymer battery located within the patch.

The resulting patch is an innovative and unique pressure sensing device that can be easily and safely placed on a patients' pressure point, and wirelessly alert providers to critical patient pressures associated with ischemia and pressure injury formation.

In various aspects, the CBPM device 102, 202, 302 is provided in the form of a flexible, waterproof pad configured for placement at an anatomical location at risk for the development of a pressure ulcer in conjunction with normal foam border dressings. Non-limiting examples of suitable anatomical locations suitable for pressure monitoring using the CBPM device include a sacrum, a hip, a heel, an occiput, a shoulder blade, an ankle, an elbow, an ear, and any other suitable location. The CBPM device may be provided in any shape suitable for conforming to the contour of a placement site without limitation. Non-limiting examples of suitable patch shapes include circular, oval, rectangular, heart-shaped, and any other suitable shape.

In some aspects, the CBPM device 102, 202, 302 includes an upper casing (FIG. 6) and a lower casing (FIG. 7) constructed of a flexible waterproof material. The upper and lower casings are constructed of any suitable material known in the art without limitation including, but not limited to, a low modulus silicone elastomer. By way of non-limiting example, the upper and lower casing may be constructed using a skin-safe silicone elastomer (Silbione RTV 4420, Elkem Silicones). In some aspects, the upper and lower casings are sealed together to define a sealed waterproof cavity containing the electronic subsystems to form a self-contained wireless CBPM device. In various aspects, the assembled casing is configured to deform in any direction without limitation, including twisting (see FIG. 8A), bending in a horizontal direction (see FIG. 8B), bending in a vertical direction (see FIG. 8C), or bending in any other direction without limitation.

In various aspects, the CBPM device 102, 202, 302 includes an array 106 of pressure sensors 116 configured to obtain pressure readings over the anatomical region underlying the patch. In various aspects, the array of pressure sensors may include at least two sensors, at least three sensors, at least four sensors, at least five sensors, at least six sensors, at least seven sensors, at least eight sensors, at least nine sensors, and at least ten sensors. In one exemplary aspect, the array of pressure sensors includes at least seven pressure sensors. In some aspects, the CBPM device further includes additional sensing elements for monitoring other aspects of the patient, including, but not limited to, a temperature sensor as illustrated in FIGS. 3 and 4.

The array 106 of pressure sensors 116 may be arranged in any suitable pattern without limitation. In some aspects, the array of pressure sensors may be arranged in at least two rows. Each row of the pressure sensor array may contain equal numbers of pressure sensors or may contain different numbers of pressure sensors. In various aspects, the number of pressure sensors in each row of the array of pressure sensors may be one sensor, two sensors, three sensors, four sensors, five sensors, or more. In other aspects, the array of pressure sensors may further be arranged in rows aligned as columns, or the rows of pressure sensors may be offset.

Each pressure sensor 116 in the array 106 of pressure sensors may be any suitable design of pressure sensor without limitation. In various aspects, each pressure sensor is configured to continuously detect pressures ranging from 0 mm Hg to about 100 mm Hg or more. In some aspects, each pressure sensor is configured to continuously detect pressures ranging from 0 mm Hg to about 400 mm Hg. Non-limiting examples of suitable pressure sensors include force-sensitive resistor (FSR) elements.

In various aspects, the array 106 of pressure sensors 116 and other electronic subsystems of the CBPM device 102, 202, 302 are mounted to a thin flexible printed circuit board (fPCB) platform 206. Conventional rigid circuit boards and hard plastic enclosures frustrate soft, conformal mounting of the CBPM device to the patient, with potential consequences in reduced patient comfort and reduced accuracy of pressure readings. In various aspects, the CBPM device may include any suitable fPCB materials known in the art without limitation. In some aspects, the fPCB platform is constructed using conductive and nonconductive flexible polymers. In one exemplary aspect, the fPCB includes a polyimide middle layer and patterned polyimide copper layers on top and bottom surfaces that serves as the mounting platform for all electronic components. By way of non-limiting example, the fPCB may include a 75-μm-thick polyimide middle layer and 18-μm-thick patterned polyimide copper layers on top and bottom surfaces.

In various aspects, the fPCB may be provided as a single continuous surface or as two or more separate surfaces interconnected by flexible, conductive interconnects. In some aspects, the fPCB is provided as a first section and a second section interconnected by flexible conductive interconnects. In these aspects, the first section is configured to serve as the mounting platform for the non-sensing electronic subsystems of the CBPM device including, but not limited to, a controller and a power source. The second section is configured to serve as the mounting platform for the sensing subsystems of the CBPM device including, but not limited to, the pressure sensor array. In some aspects, the electronic elements of the CBPM device including, but not limited to, the pressure sensors, the power source, the controller, the wireless charging unit, and the wireless communication sub-system may be operatively coupled using flexible interconnects. Non-limiting examples of suitable flexible interconnects include serpentine interconnects as illustrated in FIGS. 3 and 4.

In various additional aspects, the CBPM device 102, 202, 302 further includes a controller 108 to coordinate the operation of the various other electronic subsystems of the CBPM device to monitor tissue pressures as described herein. The selection of a controller for use in the disclosed wireless probe may tradeoff between enhanced data sampling rates and reduced power consumption. Without being limited to any particular theory, high sampling rates provide real-time, high-quality pressure measurements within a short time window in support of clinical decisions based on pressures measured by the CBPM device, but at the expense of higher power consumption. In various aspects, the controller operates the electrical subsystems of the CBPM device to support obtaining and analyzing pressures about every ten seconds or less. In various aspects, the controller produces a plurality of control signals configured to operate each pressure sensor of the pressure sensor array, to acquire signals from the pressure sensors, and to communicate the pressure sensor measurements wirelessly to a computing device or cloud-based storage system for data storage, analysis, and display. The wireless probe may include any suitable controller without limitation including, but not limited to, a microcontroller. Non-limiting examples of suitable microcontrollers include an Arm Cortex-M4F processor with a multi-channel analog to digital converter system (ADC). In some aspects, the microcontroller may further provide for wireless data transmission of data to a computing device or cloud-based storage device in accordance with any suitable wireless transmission protocol including, but not limited to, a Bluetooth protocol or a near field communication (NFC) protocol. In one exemplary aspect, the microcontroller may include Bluetooth Low Energy (BLE) data transmission technology. In one exemplary aspect, the CBPM device includes a commercially available microcontroller (nRF52832, Nordic Semiconductor) with a Bluetooth 4.0 module.

In various aspects, the electronic subsystems of the CBPM device 102, 202, 302 further include a power source 110 to provide power to the pressure sensors, the controller, and/or the wireless transmission module. Without being limited to any particular theory, battery lifetime contributes to the continuous and timely monitoring of tissue pressures in clinical settings. Continuous CBPM device operation over at least 5 days or more provides for non-interrupted monitoring of tissue pressures during hospitalization without the need for changing the CBPM device or battery, which reduces the personnel workload, improves the patient experience, and ensures monitoring reliability. The wireless CBPM device may include any suitable power source without limitation. Non-limiting examples of suitable power sources include batteries. In various aspects, a power source with a relatively high energy density may be selected to reduce the size of the CBPM device. In various other aspects, the power source includes sufficient capacity to support the continuous operation of the electrical subsystems of the wireless CBPM device for about five days or more. In one aspect, the power source is a battery with a capacity of at least 60 mAh. In some aspects, the power source may be rechargeable using any suitable remote recharging methods known in the art without limitation. By way of non-limiting example, the CBPM device includes. In one exemplary aspect, the wireless recharging module includes planar coils and associated circuitry configured to support wireless charging at a frequency of about 13.56 MHz, as illustrated in FIG. 2.

In various aspects, CBPM systems 100 are disclosed that include a computing device and/or cloud-based data storage systems operatively coupled to any of the CBPM devices 102, 202, 302 described above. The computing device (e.g., monitoring device 104) may provide any one or more of at least several functions of the CBPM sensing system including, but not limited to receiving and logging signals measured by the pressure sensor array of the CBPM device, and transforming the signals into measures of tissue pressures. The computing device may further display the measures of tissue pressures to a practitioner in real-time, and may further produce an alarm if the measurement of tissue pressures indicates a situation requiring intervention by the practitioner including, but not limited to, repositioning the patient. By way of non-limiting example, a computing device operatively coupled to a CBPM device may produce an alert if a parameter indicative of tissue pressure exceeds a threshold maximum pressure or a maximum cumulative pressure dosage indicative of an elevated risk of a pressure injury to a tissue.

Figure 5:
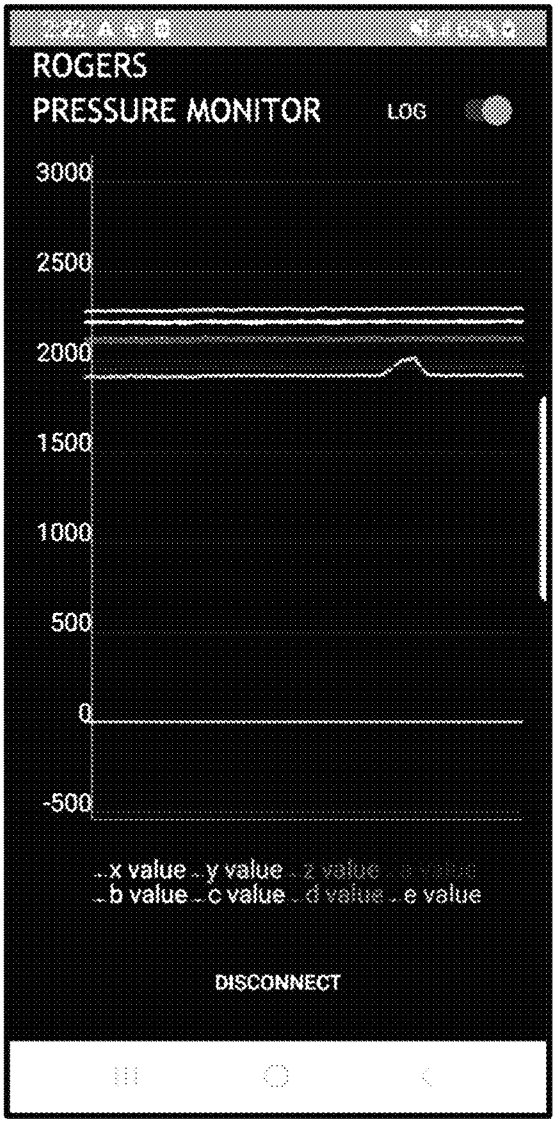
FIG. 5 is a screenshot of an app showing the outputs of the sensors of the CBPM device shown in FIG. 4.

In various aspects, the computing device of the CBPM system 100 may be any suitable computing device without limitation including, but not limited to, a computer, a server, a cellular phone, a tablet, and any other suitable computing device. In additional aspects, the system may include a data storage device including, but not limited to, a cloud-based storage device. In various aspects, the CBPM system may be configured to transmit data indicative of tissue pressures to an electronic medical record (EMR). In some aspects, the CBPM system may be configured to issue alerts to a practitioner via any suitable device typically used by a clinical practitioner. In some aspects, the CBPM system may display alerts via a tablet or other computing device at the bedside of the patient. In other aspects, the CBPM system may display alerts to hospital issued ASCOM phones or other practitioner communication devices via the EMR. By way of non-limiting examples, FIG. 5 is an image of a display on a computing device (e.g., monitoring device 104) of the readings from the pressure sensor array of a CBPM device. In some aspects, the displayed readings may be color-coded to indicate whether the pressure readings are indicative of potential tissue injury.

Figure 21:
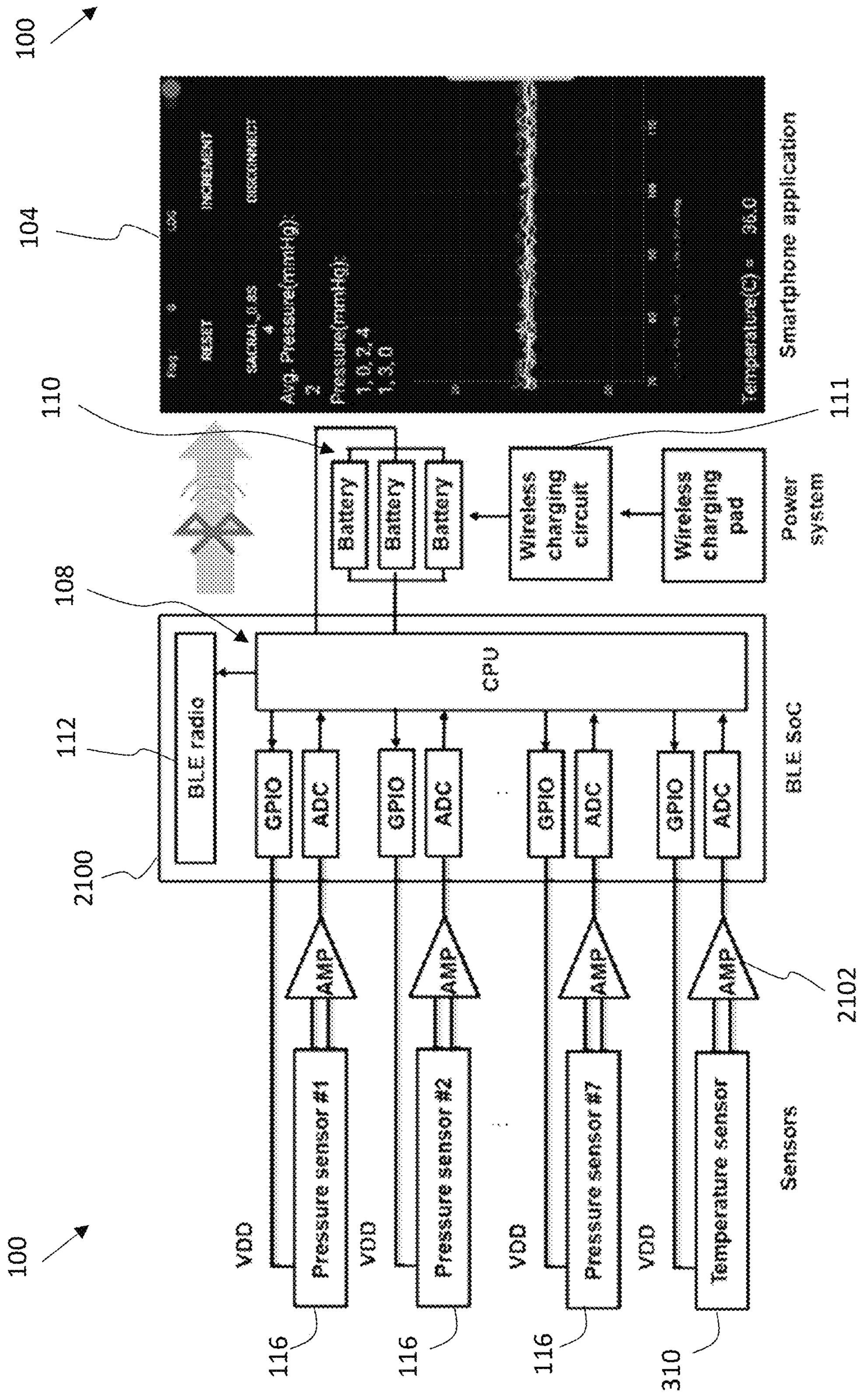
FIG. 21 is a diagram of a portion of an example CBPM system.

FIG. 21 is a diagram of a portion of an example CBPM system that may be used as the CBPM system 100 shown in FIG. 1. In this example, the communication interface 112 and the controller 108 are integrated in a Bluetooth® low energy (BLE) system on a chip (SoC) 2100. Each of the pressure sensors 116 in the array 106, and the temperature sensor 310 is coupled to the BLE SoC 2100 by an amplifier 2102. The analog output of each sensor is received by a separate analog to digital converter (ADC) 2104 and the converted digital signal is provided to the processor 118, which converts the signals to the corresponding pressures and temperature. The sensed pressures are then output by the controller 108 (using the communication interface) for display on the monitoring device 104.

Definitions and methods described herein are provided to better define the present disclosure and to guide those of ordinary skill in the art in the practice of the present disclosure. Unless otherwise noted, terms are to be understood according to conventional usage by those of ordinary skill in the relevant art.

The methods and algorithms of the disclosure may be enclosed in a controller or processor. Furthermore, methods and algorithms of the present disclosure, can be embodied as a computer-implemented method or methods for performing such computer-implemented method or methods, and can also be embodied in the form of a tangible or non-transitory computer-readable storage medium containing a computer program or other machine-readable instructions (herein "computer program"), wherein when the computer program is loaded into a computer or other processor (herein "computer") and/or is executed by the computer, the computer becomes an apparatus for practicing the method or methods. Storage media for containing such computer program include, for example, floppy disks and diskettes, compact disk (CD)-ROMs (whether or not writeable), DVD digital disks, RAM and ROM memories, computer hard drives and back-up drives, external hard drives, "thumb" drives, and any other storage medium readable by a computer. The method or methods can also be embodied in the form of a computer program, for example, whether stored in a storage medium or transmitted over a transmission medium such as electrical conductors, fiber optics or other light conductors, or by electromagnetic radiation, wherein when the computer program is loaded into a computer and/or is executed by the computer, the computer becomes an apparatus for practicing the method or methods. The method or methods may be implemented on a general-purpose microprocessor or on a digital processor specifically configured to practice the process or processes. When a general-purpose microprocessor is employed, the computer program code configures the circuitry of the microprocessor to create specific logic circuit arrangements. Storage medium readable by a computer includes medium being readable by a computer per se or by another machine that reads the computer instructions for providing those instructions to a computer for controlling its operation. Such machines may include, for example, machines for reading the storage media mentioned above.

In some embodiments, numbers expressing quantities of ingredients, properties such as molecular weight, reaction conditions, and so forth, used to describe and claim certain embodiments of the present disclosure are to be understood as being modified in some instances by the term "about." In some embodiments, the term "about" is used to indicate that a value includes the standard deviation of the mean for the device or method being employed to determine the value. In some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the present disclosure are approximations, the numerical values set forth in the specific examples are reported as precisely as practicable. The numerical values presented in some embodiments of the present disclosure may contain certain errors necessarily resulting from the standard deviation found in their respective testing measurements. The recitation of ranges of values herein is merely intended to serve as a shorthand method of referring individually to each separate value falling within the range. Unless otherwise indicated herein, each individual value is incorporated into the specification as if it were individually recited herein. The recitation of discrete values is understood to include ranges between each value.

In some embodiments, the terms "a" and "an" and "the" and similar references used in the context of describing a particular embodiment (especially in the context of certain of the following claims) can be construed to cover both the singular and the plural, unless specifically noted otherwise. In some embodiments, the term "or" as used herein, including the claims, is used to mean "and/or" unless explicitly indicated to refer to alternatives only or the alternatives are mutually exclusive.

The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and can also cover other unlisted steps. Similarly, any composition or device that "comprises," "has" or "includes" one or more features is not limited to possessing only those one or more features and can cover other unlisted features.

All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the present disclosure and does not pose a limitation on the scope of the present disclosure otherwise claimed. No language in the specification should be construed as indicating any non-claimed element essential to the practice of the present disclosure.

Groupings of alternative elements or embodiments of the present disclosure disclosed herein are not to be construed as limitations. Each group member can be referred to and claimed individually or in any combination with other members of the group or other elements found herein. One or more members of a group can be included in, or deleted from, a group for reasons of convenience or patentability. When any such inclusion or deletion occurs, the specification is herein deemed to contain the group as modified thus fulfilling the written description of all Markush groups used in the appended claims.

Any publications, patents, patent applications, and other references cited in this application are incorporated herein by reference in their entirety for all purposes to the same extent as if each individual publication, patent, patent application or other reference was specifically and individually indicated to be incorporated by reference in its entirety for all purposes. Citation of a reference herein shall not be construed as an admission that such is prior art to the present disclosure.

EXAMPLES

The following examples illustrate various aspects of the disclosure.

Example 1: Functional Testing of Pressure Monitoring Patch

To demonstrate the effectiveness of a flexible CBPM device 102, 202, 302 for monitoring tissue pressure as described herein, the following experiments were conducted.

Figure 15A:
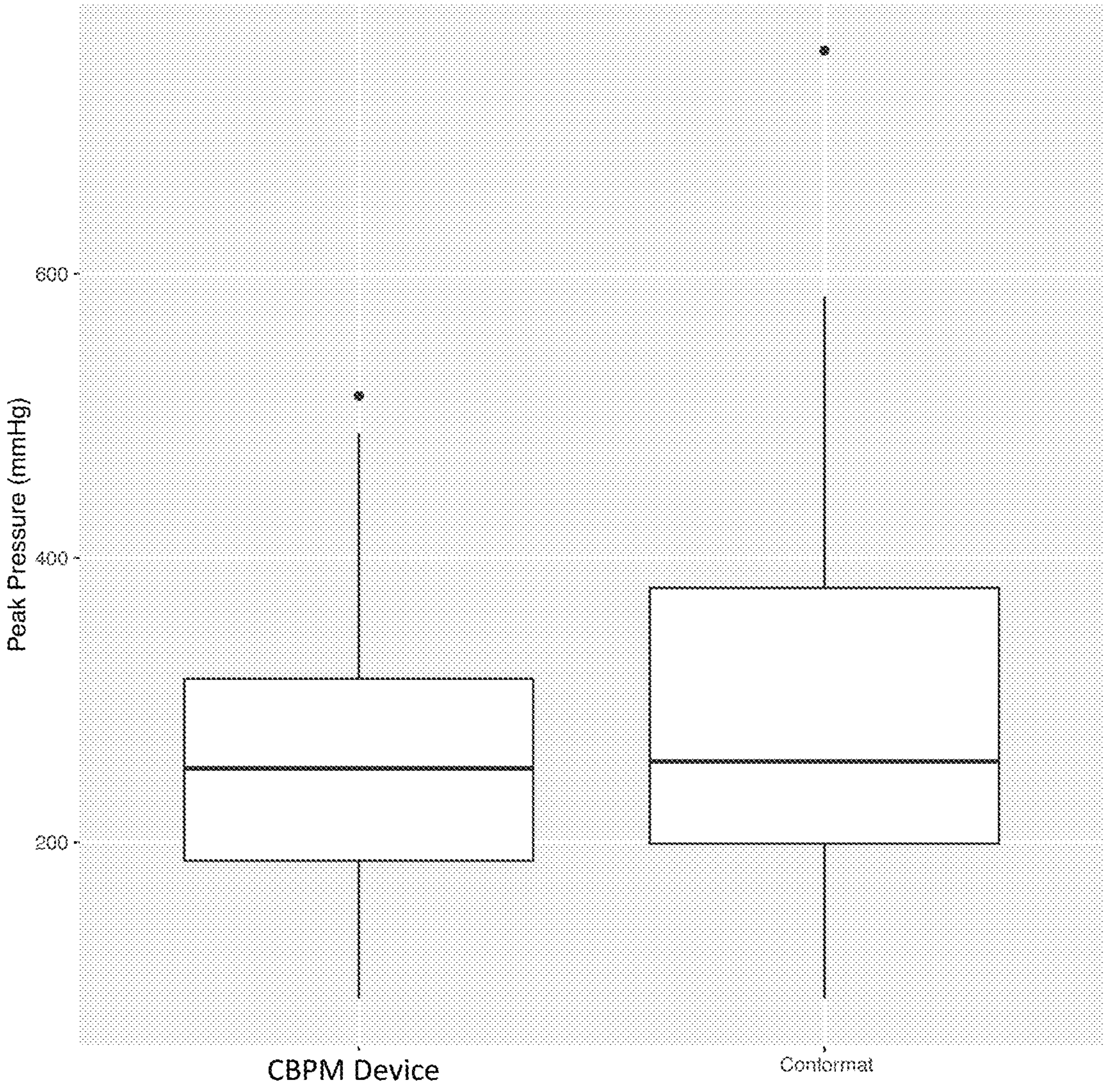
FIG. 15A is a graph comparing the peak pressures measured by a CBPM device as disclosed herein and by an existing device (CONFORMat).
Figure 15B:
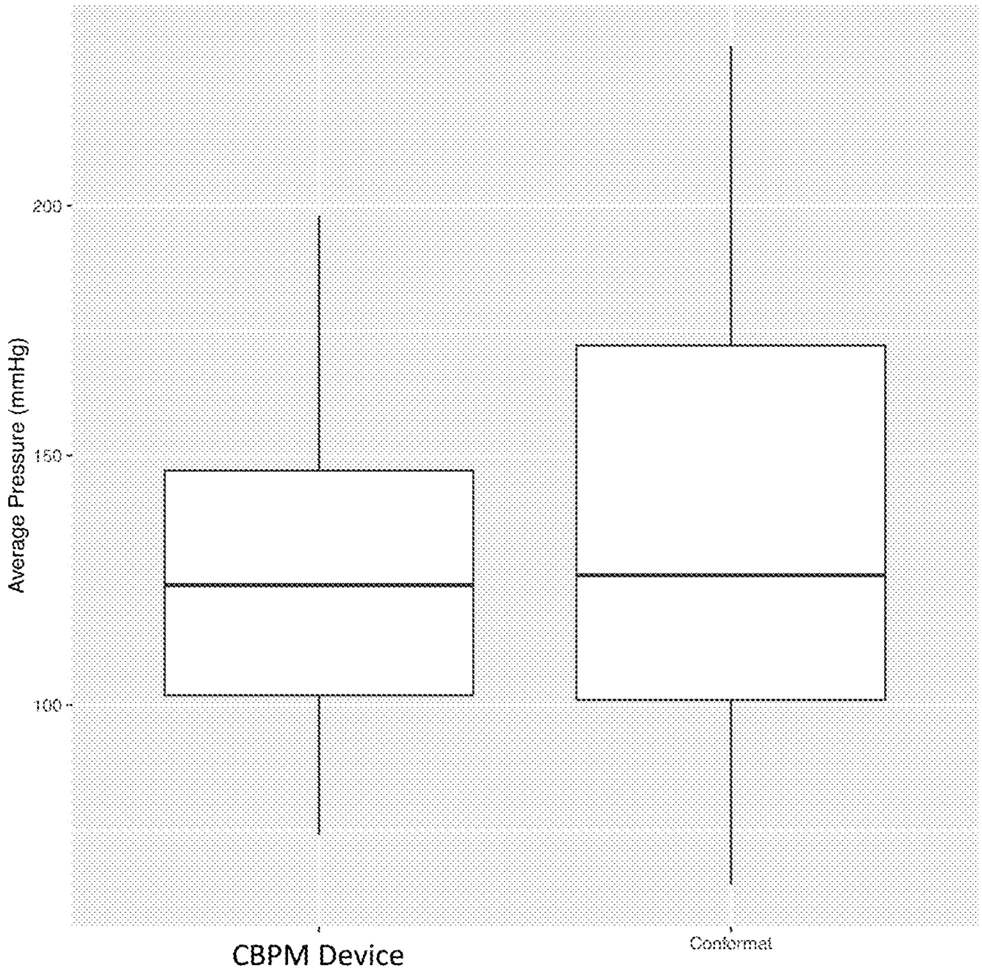
FIG. 15B is a graph comparing the average pressures measured by a CBPM device as disclosed herein and by an existing device (CONFORMat).

The performance of a flexible CBPM device similar to the CBPM device 302 described herein was compared to an off-the-shelf pressure mapping system (Tekscan, CONFORMat) using a population of healthy volunteers. Sacral pressure maps were collected for 40 participants over a short, 20-second interval using the CONFORMat system in three distinct positions. Simultaneously, pressure readings were recorded from flexible CBPM devices mounted to each participant. The CBPM device successfully recorded pressure measurements for all 40 participants and demonstrated basic functionality. The CBPM device qualitatively mirrored the pressure mapping data recorded by the CONFORMat system in all three configurations, demonstrating offloading of sacral pressure when participants progressed from a supine position to an upright position. Statistical analysis using a linear mixed-model comparing both the peak and average sacral pressure readings from the sensors in our device to that of the CONFORMat showed no statistical difference, as shown in FIGS. 15A and 15B.

The results of these experiments demonstrated that the CBPM device measured pressures in an equivalent fashion to an existing pressure mat system.

Example 2: Clinical Testing of Pressure Monitoring Patch

To demonstrate the clinical effectiveness of a flexible CBPM device for monitoring tissue pressure as described herein, the CBPM device 102, 202, 302 are used to monitor a population of patients over each patient's hospital stays. Patients with higher detected pressures are thought to be more likely to develop pressure injuries. The patients are monitored using patient-mounted CBPM devices throughout their hospital stays and will be simultaneously assessed for pressure sores at designated time intervals. Using the pressure data obtained from the CBPM devices over the course of the trial, an algorithm will be developed to define critical and at-risk pressures. This algorithm will establish the basis for a protocol for clinical interventions.

Example 3: Integration of Pressure Monitoring Patch in EMR Workflow

To demonstrate the integration of pressure data obtained using a flexible CBPM device 102, 202, 302 for monitoring tissue pressure as described herein, the following experiments were conducted. To identify points in the clinical workflow where the integration of wireless CBPM data with the electronic medical record (EMR) is optimized to alert nursing of critical pressures that require intervention based on clinical guidelines, the following experiments will be conducted. Based on pressure data obtained during a previous observational trial, an algorithm will be developed to identify pressure threshold values placing patients at risk for developing pressure injuries. The patient-specific CBPM data will be integrated into the electronic medical record.

Figure 16:
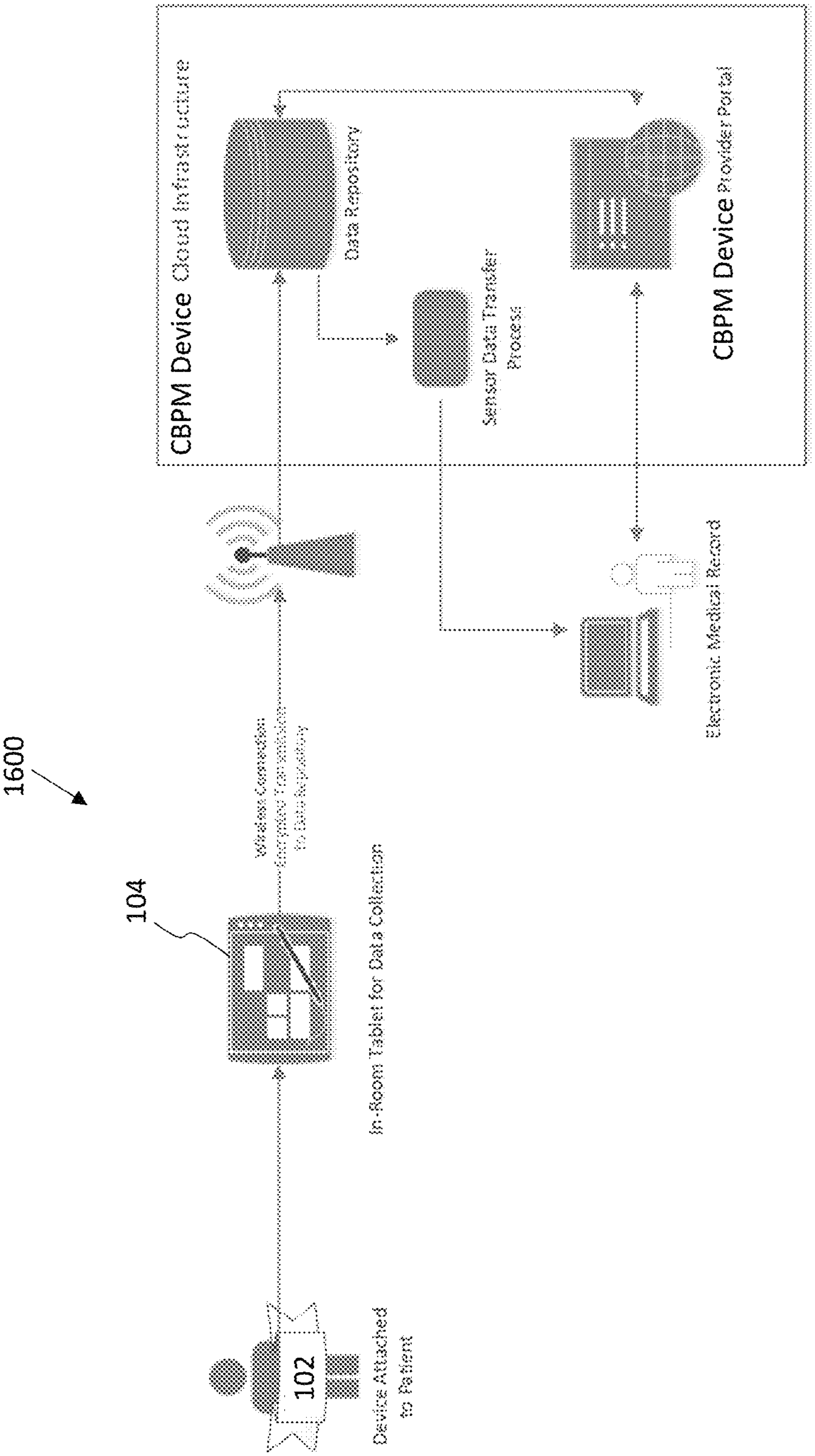
FIG. 16 is a schematic diagram illustrating the integration of the CBPM device into an Electronic Medical Record (EMR) system in accordance with one aspect of the disclosure.

The pressure monitoring device will be integrated into the medical record to send nursing staff real-time patient triggered alerts. Alerts that critical pressures have been reached and that a patient requires repositioning will be delivered within the medical records and the hospital issued ASCOM phones. FIG. 16 is a schematic diagram of a system 1600 illustrating the integration of the CBPM device 102, 202, 302 into the EMR in one aspect.

Once a CBPM device is applied to a patient, the CBPM device will be associated with the patient via the Provider Portal of the EMR. Pressure data will be sent wirelessly from the CBPM device on the patient's sacrum to a synched in-room tablet housing a data collection application. These data will be wirelessly pushed to a cloud-based HIPAA-compliant data repository. Providers will be able to visit the Provider Portal of the EMR to review summarized data pertaining to the levels and durations of pressure readings for each patient. The provider portal will be accessible as a context-integrated link within the EMR, providing access to the patient-specific view.

The highest pressure recorded per hour will be pushed to and viewable on the patient's vital sign flowsheet. The in-room tablet will also passively flash second by second pressure readings, silently highlighting critical pressures in red, and non-critical pressures in black.

An algorithm housed in the data repository will be used to identify critical pressures placing patients at risk for developing pressure injuries. If the algorithm identifies critical pressures among the pressure readings for a patient, the data repository will trigger an alert to be sent to the EMR indicating that the patient requires offloading. The medical record will also trigger a text to the ASCOM phone of the nurse assigned to that patient. Alerts will only be triggered every 15 minutes with a maximum of 4 alerts an hour. Nursing will be able to monitor pressure readings on the in-room tablet to evaluate for effective off-loading.

The HIPPA-compliant cloud will extract a limited set of information including BMI, diabetes status, and blood pressure data back into the data repository to provide information for refinement of the algorithm.

The integration of pressure data obtained using the CBPM device into the EMR and nursing alerts will integrate into the workflow and provide a positive adjunct to nursing clinical decision making when offloading patients. Open-ended focus groups of bedside providers making use of the CBPM devices will be held to assess the degree of integration of CBPM with existing clinical workflow. Nursing providers will also fill out a weekly survey to determine if the bedside tablet pressure readings are a helpful adjunct to turning practices, as well as to obtain feedback on the alert system. Lines of questioning for focus groups and weekly surveys will be directed to assess the degree of workflow integration, and the perception of a reduction in interruptions by introducing technology that standardizes workflow.

Example 4: Reduction of Pressure Injuries Using CBPM Device

To demonstrate the reduction of pressure injuries in a patient population using a CBPM device 102, 202, 302, the following experiments will be conducted. The CBPM devices described herein will be used to monitor pressures on patients within an intensive care unit and the CBPM-measured pressure will be used in an algorithm to drive patient turning in the intensive care unit, resulting in a reduction in the incidence of new pressure injuries.

Adult patients undergoing a minimum of two-hour supine surgery with an intended surgical intensive care unit stay will be eligible to participate in this study. Patients with known sacral pressure sores, previous sacral pressure sores, or those unable to consent with be ineligible. All patients will receive a CBPM device placed outside a foam barrier pad at the beginning of surgery. Pressure will be mapped during this time with no intervention. Upon arrival to the ICU, patients will be randomized to the intervention vs non-intervention groups in a 1:1 fashion. For patients randomized to the intervention group, pressure data will integrate into the medical record, as described herein, and nursing staff will perform the standard turning protocol every two hours, as well as additionally turning the patients in response to alerts associated with CBPM device readings. The bedside tablet will silently flash current sacral pressures for patients in the intervention group, with red pressures determined to be at-risk readings and black pressures safe pressures. For patients randomized to the non-intervention group, pressure data will be collected, but alerts will not be sent and pressure information will not appear in the flow sheet. The bedside tablet will also not flash any pressures for the non-intervention group patients.

A trained researcher will assess the sacrum for evidence of new pressure sores on a daily basis until discharge. This assessment will be compared to the nursing assessment that is documented per protocol in the patient record. Nursing staff will be asked to fill out a short survey on the in-room tablet at the end of each shift to allow researchers to assess compliance with the standardized turning protocol, the additional alerts, and the usefulness of the bedside tablet pressure readings.

An ordinary least squares (OLS) regression analysis on the cohort comparing the ratio of pressure injuries between experimental and control arms will be performed. This multivariable regression approach will control for key patient demographics such as age, sex, and race. The OLS regression analysis will quantify the reduction of incident pressure injuries in medical records as a result of pressure monitoring using the CBPM device. It is anticipated that pressure sensing using the CBPM device will reduce incident pressure injuries by 25% during the experimental period.

Example 5: Cost-Effectiveness of CBPM Device

To demonstrate the cost-effectiveness of CBPM devices 102, 202, 302, the following experiments were conducted.

Hospitals are often limited in their ability to invest in new technology since the price often outweighs the benefit, at least in the short term. In the long run, hospitals could perhaps justify the investment in technology, however, they must withdraw resources from other areas in order to reach a point of return on investment (ROI). It is anticipated that the use of CBPM devices in the operating room will be cost-effective and will provide an almost immediate ROI by saving on the cost of nursing time and cost-consequences of pressure injuries through investment in a low-cost technology.

The costs for implementation of the CBPM devices will be estimated based on the expected list price of the technology combined with a commonly used prophylactic border sacral dressing and nursing time to apply the technology on the patient. Costs for integrating the CBPM sensor technology with the existing electronic medical record system will also be estimated. Existing information on the cost of nursing time for manual repositioning as well as the cost of pressure injury care in the acute and post-acute settings will be obtained and compared to the estimated costs of implementing the use of the CBPM devices. Effectiveness will be measured in terms of pressure injuries avoided and a gold standard measure of health utility, quality-adjusted life years (QALYs).

The cost-effectiveness of the CBPM pressure sensing technology will be captured using the framework of a Markov model. This model will provide information on transitioning health states exemplified by the pressure injury staging guidelines (i.e. stage 1 bruising; stage 2 open wounds; and stages 3, 4 and unstageable full-thickness wounds). The model will calculate the cost-effectiveness of integrated pressure sensors in hospitals over 1 year based on the health system and U.S. societal perspectives. This economic evaluation will generate an incremental cost-effectiveness ratio (ICER) to express the net monetary benefit of pressure sensing technology after 1 year at a willingness-to-pay threshold of $100,000/QALY. The ROI of the CBPM pressure sensing technology will also be calculated based on costs for a series of different sized hospitals.

Having described the present disclosure in detail, it will be apparent that modifications, variations, and equivalent embodiments are possible without departing the scope of the present disclosure defined in the appended claims. Furthermore, it should be appreciated that all examples in the present disclosure are provided as non-limiting examples.

What is claimed is:

1. A continuous bedside pressure monitoring (CBPM) device comprising:

an array of pressure sensors;

a controller including a processor and a memory, the controller operatively coupled to the array of pressure sensors;

a communication interface operatively coupled to the controller;

a flexible printed circuit board (fPCB) including two or more separate surfaces interconnected by flexible, conductive interconnects, wherein the array of pressure sensors, the controller, and the communication interface are electrically mounted on the fPCB; and a sealed, waterproof, flexible housing comprising an upper casing and a lower casing, the upper casing sealed to the lower casing to enclose the fPCB and the array of pressure sensors, the controller, and the communication interface mounted on the fPCB, the housing configured for attaching the CBPM device to a patient's body, the upper casing and the lower casing each having a plurality of holes defined therethrough, wherein each hole of the upper casing has a corresponding hole of the lower casing, a perimeter of each hole of the upper casing is sealed to a perimeter of the corresponding hole of the lower casing to define a sealed opening through the housing and each sealed opening is defined through the housing at a different location where none of the fPCB, the array of pressure sensors, the controller, or the communication interface are located.

2. The CBPM device of claim 1, wherein the memory stores instructions that, when executed by the processor, configure the controller to:

detect a pressure applied to each pressure sensor of the array of pressure sensors; and transmit the detected pressure applied to each pressure sensor to a monitoring device using the communication interface.

3. The CBPM device of claim 2, wherein the instructions stored in the memory further configure the processor to continuously detect the pressure applied to each pressure sensor and to continuously transmit the detected pressure applied to each pressure sensor to the monitoring device.

4. The CBPM device of claim 2, wherein the instructions stored in the memory further configure the processor to:

continuously detect the pressure applied to each pressure sensor;

store the detected pressures applied to each pressure sensor in the memory; and periodically transmit the stored detected pressures applied to each pressure sensor to the monitoring device.

5. The CBPM device of claim 1, further comprising a power source coupled to the controller to provide power for the controller, the power source located within the flexible housing.

6. The CBPM device of claim 5, wherein the power source comprises a rechargeable battery.

7. The CBPM device of claim 6, further comprising a charging interface coupled to the rechargeable battery to provide power to recharge the rechargeable battery.

8. The CBPM device of claim 7, wherein the charging interface comprises a planar coil for wireless charging.

9. The CBPM device of claim 1, wherein each pressure sensor of the array of pressure sensors comprises a force sensitive resistor.

10. The CBPM device of claim 1, wherein the communication interface comprises a wireless communication interface.

11. The CBPM device of claim 10 wherein the wireless communication interface comprises a wireless transceiver operating according to a Bluetooth specification.

12. The CBPM device of claim 1, further comprising a temperature sensor within the flexible housing and operatively coupled to the controller and to the power source.

13. The CBPM device of claim 1, wherein the sealed, waterproof, flexible housing comprises silicone.

14. A continuous bedside pressure monitoring (CBPM) system, the system comprising:

a CBPM device including:

an array of pressure sensors;

a controller including a processor and a memory, the controller operatively coupled to the array of pressure sensors;

a communication interface operatively coupled to the controller;

a flexible printed circuit board (fPCB) including two or more separate surfaces interconnected by flexible, conductive interconnects, wherein the array of pressure sensors, the controller, and the communication interface are electrically mounted on the fPCB; and a sealed, waterproof, flexible housing comprising an upper casing and a lower casing, the upper casing sealed to the lower casing to enclose the fPCB and the array of pressure sensors, the controller, and the communication interface mounted on the fPCB, the housing configured for attaching the CBPM device to a patient's body, the upper casing and the lower casing each having a plurality of holes defined therethrough, wherein each hole of the upper casing has a corresponding hole of the lower casing, a perimeter of each hole of the upper casing is sealed to a perimeter of the corresponding hole of the lower casing to define a sealed opening through the housing and each sealed opening is defined through the housing at a different location where none of the fPCB, the array of pressure sensors, the controller, or the communication interface are located; and a monitoring device operatively coupled to the CBPM device.

15. The CBPM system of claim 14, wherein the CBPM device and the monitoring device are operatively coupled by a wireless connection.

16. The CBPM system of claim 15, wherein the monitoring device comprises at least one of a personal computer, a server system, a tablet, a cellular telephone, a cloud-based storage system, an electronic medical record (EMR) system, or any combination thereof.

17. The CBPM system of claim 14, wherein the monitoring device is configured to store signals indicative of pressures detected by the array of pressure sensors and to transform at least one of the pressures detected by the array of pressure sensors into a parameter indicative of a potential pressure injury to tissue adjacent the CBPM.

18. The CBPM system of claim 17, wherein the parameter indicative of the potential pressure injury comprises at least one of a tissue pressure exceeding a pressure injury threshold and a cumulative pressure dosage exceeding a dosage threshold.

* * * * *